US012653387B2

(12) United States Patent
Dayton et al.

(10) Patent No.: US 12,653,387 B2
(45) Date of Patent: *Jun. 16, 2026

(54) DEVICES, SYSTEMS, AND METHODS FOR LOCATING A BODY LUMEN

(71) Applicants: BOSTON SCIENTIFIC SCIMED, INC., Maple Grove, MN (US); BRUSSELS MEDICAL DEVICE CENTER, Brussels (BE)

(72) Inventors: Peter L. Dayton, Brookline, MA (US); Nicolas Cauche, Brussels (BE); Cecilia Delattre, Ganshoren (BE); Marc A. Barthet, Marseilles (FR); Jean-Michel Gonzalez, Fuveau (FR); Louis J. Barbato, Franklin, MA (US); Eric F. Brown, Wilmington, MA (US); John Nguyen, Stoughton, MA (US); John T. Favreau, Charlton, MA (US); Marcia Nardone, Northborough, MA (US)

(73) Assignees: Boston Scientific Scimed, Inc., Maple Grove, MN (US); Brussels Medical Device Center, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/918,269

(22) Filed: Oct. 17, 2024

(65) Prior Publication Data

US 2025/0031952 A1 Jan. 30, 2025

Related U.S. Application Data

(63) Continuation of application No. 17/034,026, filed on Sep. 28, 2020, now Pat. No. 12,150,621.

(Continued)

(51) Int. Cl.
*A61B 1/01* (2006.01)
*A61B 1/00* (2006.01)
(Continued)

(52) U.S. Cl.
CPC ............ *A61B 1/01* (2013.01); *A61B 1/00082* (2013.01); *A61B 1/00094* (2013.01);
(Continued)

(58) Field of Classification Search
CPC ... A61B 1/01; A61B 1/00082; A61B 1/00094; A61B 1/00119; A61B 1/0684;
(Continued)

(56) References Cited

U.S. PATENT DOCUMENTS 8,027,710 B1 9/2011 Dannan
10,356,378 B2 7/2019 Hirota
(Continued)

FOREIGN PATENT DOCUMENTS

CN 106852708 A 6/2017
EP 3178432 A1 6/2017
(Continued)

OTHER PUBLICATIONS

International Search Report and Written Opinion for the International Application No. PCT/US2020/052995, mailed Dec. 4, 2020. (25 Pages).

*Primary Examiner* — Peter Luong
(74) *Attorney, Agent, or Firm* — Seager, Tufte & Wickhem, LLP

(57) ABSTRACT

This disclosure relates generally to medical devices, systems, and methods for locating devices and/or anatomy during medical procedures. More particularly, in some embodiments, the disclosure relates to medical device and/ or anatomy locating devices, access devices, and systems and methods thereof, for use during, e.g., gastrojejunostomy procedures. In an aspect, a medical device locator may include an elongate member (such as sheath or guidewire) having a proximal end, a distal end, a longitudinal axis, and a length extending along the longitudinal axis. A location (Continued)

device may be disposed along the length of the elongate member.

20 Claims, 22 Drawing Sheets

Related U.S. Application Data

(60) Provisional application No. 62/954,875, filed on Dec. 30, 2019.

(51) Int. Cl.
  *A61B 1/06*       (2006.01)
  *A61B 1/273*      (2006.01)
  *A61B 1/31*       (2006.01)
  *A61B 90/00*      (2016.01)

(52) U.S. Cl.
  CPC ........ *A61B 1/00119* (2013.01); *A61B 1/0684* (2013.01); *A61B 1/2736* (2013.01); *A61B 1/31* (2013.01); *A61B 2090/3945* (2016.02)

(58) Field of Classification Search
  CPC ....... A61B 1/2736; A61B 1/31; A61B 1/3132; A61B 1/018; A61B 2090/3945; A61B 2090/062; A61B 2090/0807; A61B 2090/0811; A61B 2090/306; A61B 2090/309; A61B 2090/3937; A61B 2090/3966; A61B 17/12099; A61B 17/12172; A61B 17/1114; A61B 2017/00278; A61B 2017/00358; A61B 2017/00818; A61B 2017/00867; A61B 2017/1139; A61B 5/061; A61B 90/30; A61F 5/0013; A61F 5/0079
  See application file for complete search history.

(56) References Cited

U.S. PATENT DOCUMENTS

| | | | |
|---|---|---|---|
| 12,150,621 B2 * | 11/2024 | Dayton | .................. A61B 5/061 |
| 2005/0119527 A1 | 6/2005 | Banik et al. | |
| 2005/0228452 A1 | 10/2005 | Mourlas et al. | |
| 2008/0045800 A2 | 2/2008 | Farr | |
| 2008/0108869 A1 | 5/2008 | Sanders et al. | |
| 2008/0194973 A1 | 8/2008 | Imam | |
| 2009/0129051 A1 | 5/2009 | Bausewein et al. | |
| 2011/0230722 A1 | 9/2011 | Kudo et al. | |
| 2014/0073858 A1 | 3/2014 | Sherwinter | |
| 2016/0143522 A1 | 5/2016 | Ransbury et al. | |
| 2016/0143552 A1 | 5/2016 | Lee et al. | |
| 2017/0290693 A1 | 10/2017 | Nelson et al. | |
| 2018/0271530 A1 | 9/2018 | Dayton et al. | |
| 2019/0298401 A1 | 10/2019 | Gupta et al. | |
| 2019/0298559 A1 | 10/2019 | Gupta et al. | |
| 2020/0129318 A1 | 4/2020 | Duval et al. | |
| 2020/0187946 A1 | 6/2020 | Baron et al. | |
| 2021/0100528 A1 | 4/2021 | Dayton et al. | |
| 2021/0196106 A1 | 7/2021 | Dayton et al. | |
| 2022/0061848 A1 | 3/2022 | Saenz Villalobos et al. | |

FOREIGN PATENT DOCUMENTS

| | | |
|---|---|---|
| JP | 2018171544 A | 11/2018 |
| JP | 2019048172 A | 3/2019 |
| JP | 7443528 B2 | 3/2024 |
| WO | 2015164437 A1 | 10/2015 |
| WO | 2016185733 A1 | 11/2016 |
| WO | 2017106706 A1 | 6/2017 |
| WO | 2019040461 A1 | 2/2019 |
| WO | 2019140097 A1 | 7/2019 |

* cited by examiner

1

DEVICES, SYSTEMS, AND METHODS FOR LOCATING A BODY LUMEN

PRIORITY

This application is a continuation of and claims the benefit of the earlier filing date of U.S. patent application Ser. No. 17/034,026, filed Sep. 28, 2020, which claims the benefit of priority under 35 USC § 119 to U.S. Provisional Patent Application Ser. No. 62/954,875, filed Dec. 30, 2019, and which applications are incorporated herein by reference in their entireties for all purposes. Any and all priority claims identified in the Application Data Sheet, or any correction thereto, are hereby incorporated by reference under 37 C.F.R. § 1.57.

FIELD

This disclosure relates generally to medical devices, systems, and methods for locating devices and/or anatomy during medical procedures. More particularly, in some embodiments, the disclosure relates to medical device and/or anatomy locating devices, access devices, and systems and methods thereof, for use during gastrojejunostomy procedures.

BACKGROUND

Various health issues, e.g., obesity and diabetes, affect a growing population and may cause additional diseases, increasing risk of a patient's health. Surgical procedures such as bariatric surgery, e.g., to restrict a portion of a stomach and/or bypass portions of the intestine and/or other portions of the gastrointestinal (GI) tract, may be an option for certain patients with these and/or other health issues. These types of procedures may have significant side effects, e.g., such as enteric hormonal changes, and may be invasive surgical procedures with associated complications, tissue trauma, anastomotic leaks, infections, and/or additional surgeries to modify the initial surgery, e.g., to reorient the placement of a bypass device, which in some instances may put patients at increased risk.

Accordingly, it may be desirable for less invasive medical devices, systems, and related methods for treating the GI tract and/or bypassing portions of the intestine, to reduce complications associated with treating some of these and other health issues. This disclosure may solve one or more of these problems or other problems in the art.

SUMMARY

According to an aspect, a medical device locator may comprise an elongated member including a location device at a distal end of the elongated member. The location device may include at least one light emitting diode (LED), and wherein the at least one LED may be configured to be actuated to emit a light having wavelengths corresponding to a green light and a red light.

The location device may include a sidewall, a proximal end wall at a proximal end of the sidewall, and a distal end wall at a distal end of the sidewall, wherein the sidewall, the proximal end wall, and the distal end wall may define a cavity, and wherein the at least one LED may be disposed within the cavity.

The sidewall may include a transparent material or a semi-transparent material, and at least one of the proximal end wall or the distal end wall may include one or more of an opaque material or a light attenuating material.

The elongated member may include a fluid lumen extending from a proximal end of the elongated member to a distal end of the elongated member. A plurality of holes may be disposed in a sidewall of the elongated member and fluidly connected to the fluid lumen.

A vacuum device and a fluid containment device may be connected to the elongated member, wherein each of the vacuum device and the fluid containment device may be in fluid communication with the fluid lumen at the proximal end of the elongated member, and wherein the vacuum device may be configured to create suction within the fluid lumen such that a fluid from a body may be configured to flow through the plurality of holes and along the fluid lumen to the fluid containment device.

The elongated member may include a central lumen configured to receive a guidewire.

The location device may include a balloon at the distal end of the elongated member, and the balloon may be configured to be inflated.

The balloon may include a transparent or a semi-transparent material, the at least one LED may be disposed on a surface of the elongated member, and the light emitted from the LEDs may be configured to be transmitted through the balloon.

The balloon may be disposed on a first side of the elongated member, and the at least one LED may be disposed on a circumferentially opposite side of the elongated member from the balloon.

The at least one LED may include a plurality of LEDs. The plurality of LEDs may be disposed about a circumference of the balloon.

The elongated member may include an elongated member main body and an elongated member distal tip, wherein a proximal end of the elongated member distal tip may be connected to a distal end of the elongated member main body by a plurality of wires, and wherein an LED of the at least one LED may be attached to each wire from the plurality of wires.

An actuation wire may be attached to the elongated member distal tip, wherein the actuation wire may be configured to move proximally relative to the elongated member main body, and wherein the LEDs may be configured to move radially outward when the actuation wire moves the elongated member distal end proximally relative to the elongated member main body.

The at least one LED may be configured to alternatively emit the green light and the red light.

The at least one LED may be configured to emit the green light and the red light in a pulsed manner.

A system with the medical device locator may include an endoscope having an imaging device and an end effector which may extend from a distal end of the endoscope, wherein the imaging device may be configured to detect the light from the locator having wavelengths corresponding to the green light and to the red light emitted from the at least one LED.

According to another aspect, a method may comprise inserting an endoscope into a body and advancing the endoscope to a stomach of the body, wherein a distal end of the endoscope includes a camera, inserting an elongated member into the body, wherein a distal end of the elongated member includes at least one light emitting diode (LED), advancing the elongated member through the stomach and into a small bowel of the body, activating the at least one LED to emit a first light having a first wavelength, detecting the first light with the camera, activating the at least one LED to emit a second light having a second wavelength, different from the first wavelength, and detecting the second light with the camera.

The method may further include creating one or more of an incision in a wall of the stomach and a wall of the small bowel corresponding to the location of the at least one LED.

The first light may have a wavelength corresponding to a red light, and the second light may have a wavelength corresponding to a green light.

According to yet another aspect, a method may comprise inserting an endoscope into a body and advancing the endoscope to a stomach of the body, wherein a distal end of the endoscope includes a camera, inserting an elongated member into the body, wherein a distal end of the elongated member includes a location device including at least one light emitting diode (LED), advancing the elongated member through the stomach and into a small bowel of the body, creating an incision in a wall of the stomach, advancing the endoscope through the incision in the wall of the stomach, activating the at least one LED to red light, detecting the red light with the camera, activating the at least one LED to emit green light, detecting the green light with the camera, creating an incision in a wall of the small bowel, based on at least one of detecting the red light and detecting the green light, and placing a stent to connect the wall of the stomach and the wall of the small bowel. The at least one LED may be activated to emit the red light and the green light in a pulsed manner.

In another aspect, medical device locator may include an elongate member having a proximal end, a distal end, a longitudinal axis, and a length extending along the longitudinal axis. A location device may be disposed along the length of the elongate member.

In various embodiments described herein and otherwise within the scope of the present disclosure, the elongate member may be a tubular sheath extendable about a catheter. A plurality of illuminating members may be disposed along the length of the elongate member. The location device may include an inflatable member disposed along the distal end of the elongate member. An inflation lumen may extend along the length of the elongate member in fluid communication with the inflatable member. The plurality of illuminating members may include LEDs disposed along the length of the elongate member, the LEDs actuatable to emit a light having a wavelength corresponding to a green light or a red light. The location device may include one or more LEDs of the plurality of illuminating members at a terminal distal point of the illuminating members along the elongate member identifiable to locate the medical device. The location device may include one or more LEDs of the plurality of illuminating members leading up to the terminal distal point. A plurality of leads may be in electrical communication with the plurality illuminating members extending along the elongate member. A controller may be electrically communicative with the plurality of leads extending along the elongate member. The controller may be configured to selectively actuate portions of the plurality of illuminating members in a distal direction along the length of the elongate member. The controller may be configured to actuate a selected one or more LEDs of the plurality of illuminating members sequentially in a distal direction along the length of the elongate member. The controller may be configured to actuate all of the illuminating members of the plurality of illuminating members except one illuminating member of the plurality of illuminating members, wherein the one illuminating member sequentially changes upon each activation of the illuminating members in a distal direction. The plurality of illuminating members may include select illuminating members along a proximal portion of the elongate member having a first wavelength and select illuminating members along a distal portion of the elongate member having a second wavelength. The plurality of illuminating members may be actuatable with a shortening frequency interval in a distal direction along the length of the elongate member. The plurality of illuminating members may be arranged along the length of the elongate member such that a density of the illuminating members increases along the length of the elongate member extending from the proximal end towards the terminal distal point along the elongate member. The plurality of illuminating members may be individually selectable and controllable as a single illuminating member or in groups of more than a single illuminating member. The plurality of illuminating members may extend along the length of the elongate member for a distance of about 50 centimeters.

In another aspect, a system for locating a medical device may include a medical device locator comprising an elongate member having a proximal end, a distal end, a longitudinal axis, and a length extending along the longitudinal axis. A location device may be disposed along the length of the elongate member. A plurality of illuminating members may be disposed along the length of the elongate member. The elongate member may be extendable within a first body lumen. A medical device may be locatable within a second body lumen. The medical device may be locatable with the medical device locator to a target position in the second body lumen opposing the location device across a tissue wall of the first body lumen and a second tissue wall of the body lumen. The plurality of illuminating members may include LEDs. A controller may be electrically coupled to the plurality of LEDs. The controller may be configured to selectively actuate the plurality of LEDs along the length of the elongate member in a distal direction.

In another aspect, a method of locating a medical device locator may include inserting an elongate member within a first body lumen. The elongate member may include a plurality of LEDs extending along a length of the elongate member. A location device may be disposed at a distal end of the elongate member. The controller may be configured to selectively actuate the plurality of LEDs along the length of the elongate member in a distal direction. The actuated plurality of LEDs may be viewable across a wall of the first body lumen to position the location device at a target position within the first body lumen. An opening may be cut across a wall of a second body lumen toward the first body lumen at the target position and cutting an opening across the wall of the first body lumen at the target position. The location device may comprise one or more LEDs of the plurality of LEDs. Viewing of the actuated plurality of LEDs may be performed from within the peritoneal cavity.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
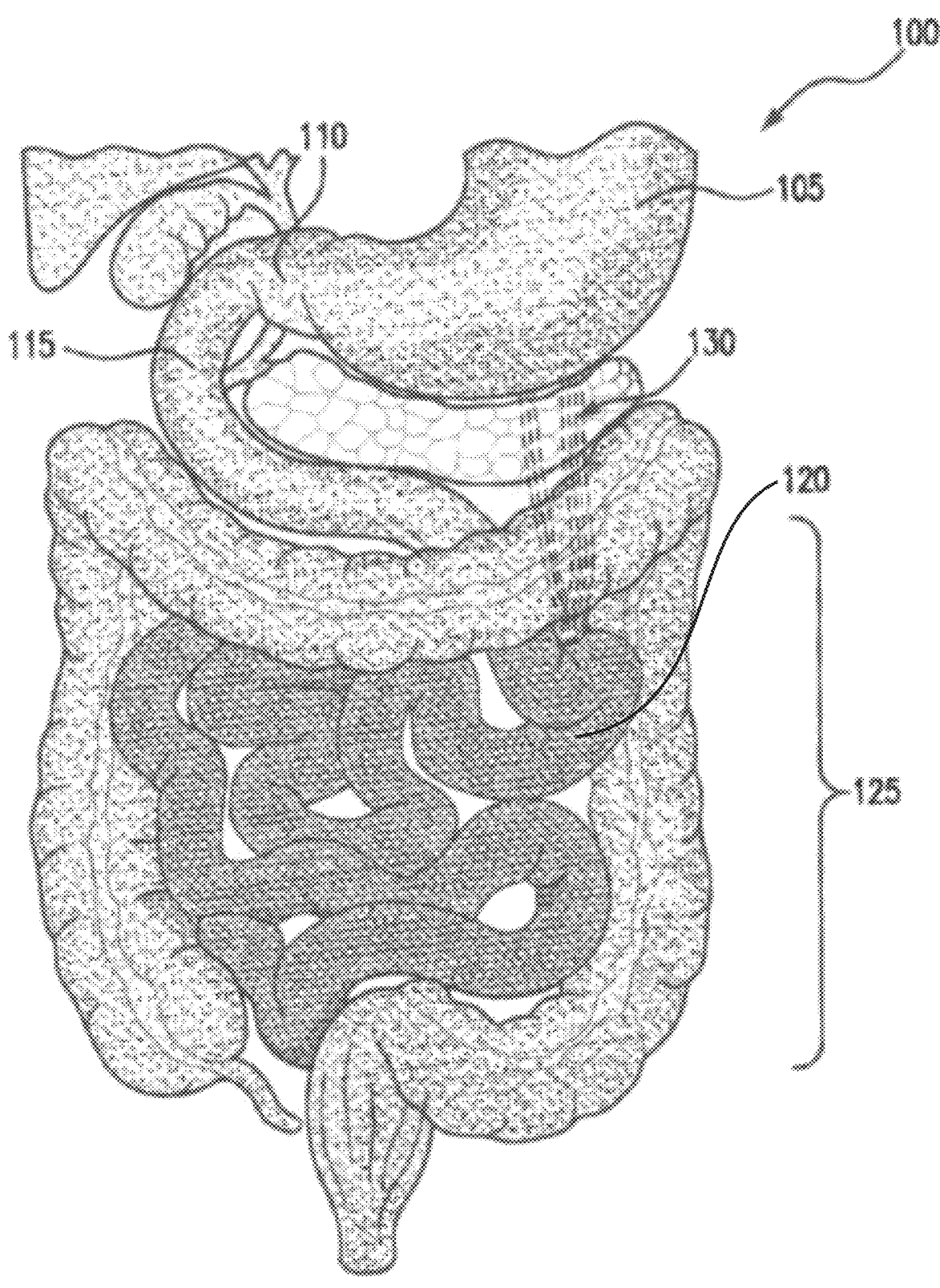
FIG. 1 illustrates a human gastrointestinal system.

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, wherein like elements are referred to with the same reference numerals.

Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Although embodiments of the present disclosure are described with specific reference to embodiments of medical device locators, and systems and methods, for locating medical devices within a specific portion of the GI tract for a particular purpose (e.g., to impact metabolism and affect weight loss), it should be appreciated that such embodiments may be used to locate a variety of configurations of such medical devices into a variety of different body lumens and/or passageways, for a variety of different purposes, including, for example, anal access to the transverse colon, ascending colon or ileum, Roux-en-Y procedures, jejunocolonic bypass procedures, jejunoileal bypass procedures, gastrectomy procedures, biliopancreatic diversion with duodenal switch (BPD-DS) procedures, gastrojejunostomy procedures, segmental colonic resection procedures, and other procedures involving the use of a medical device locator with a beacon for locating a target portion of a body lumen, so that an instrument can gain access to the lumen at the target portion by viewing the beacon from external to the lumen, and the like.

Although the present disclosure includes description of anastomoses, openings or fistulas formed in the GI tract to affect weight and absorption, the devices, systems, and methods herein could be implemented along various other portions of the GI tract, or between lumens outside of the GI tract, and for various other drainage and/or conduit purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Referring to FIG. 1, a gastrointestinal system 100 is shown. Gastrointestinal system 100 may include a stomach 105, a small bowel 125, and a pylorus 110 connecting stomach 105 to small bowel 125. Small bowel 125 includes a duodenum 115 and a jejunum 120, wherein the duodenum 115 is proximal to jejunum 120, and a junction of duodenum 115 and jejunum 120 is defined by a location of the ligament of Treitz 130 connecting to small bowel 125. As will be explained herein, an anastomosis may be created between stomach 105 and jejunum 120 to bypass pylorus 110, duodenum 115, and/or a portion of jejunum 120. In this manner, stomach content (e.g., food, liquid, and nutrients) may not be absorbed or the absorption of stomach content may be limited and/or delayed as it travels from stomach 105 through small bowel 125, which may promote patient weight loss and, in some examples, improving weight related and other health conditions, such as resolving Type 2 diabetes.

Referring to FIGS. 2A-2F, an example of an endoscopic procedure, e.g., a gastrojejunostomy, in accordance with this disclosure is shown. In a first step 200, a nasocatheter 230 may be inserted into a patient, e.g., through a nose and an esophagus, into stomach 105 and/or small bowel 125 of a patient. A distal end 235 of nasocatheter 230 may be positioned in small bowel 125 at a desired distance into jejunum 120, as determined by a medical professional and/or based on a medical procedure. Nasocatheter 230 may be advanced by peristaltic motion and/or by the medical professional by pushing on a handle associated with a proximal end of nasocatheter 230, which may cause nasocatheter 230 to move distally. As will be described herein, nasocatheter 230 may be configured to slide along a guidewire to position nasocatheter 230 in gastrointestinal system 100. In a second step 205, shown in FIG. 2B, an endoscope 240 may be inserted into stomach 105, so that a distal end 245 of endoscope 240 is positioned in a region of stomach 105 that is near distal end 235 of nasocatheter 230 located in jejunum 120, e.g., in a bottom portion of the stomach having a greater curvature and/or in the antrum portion of the stomach.

Figures 2A, 2B:
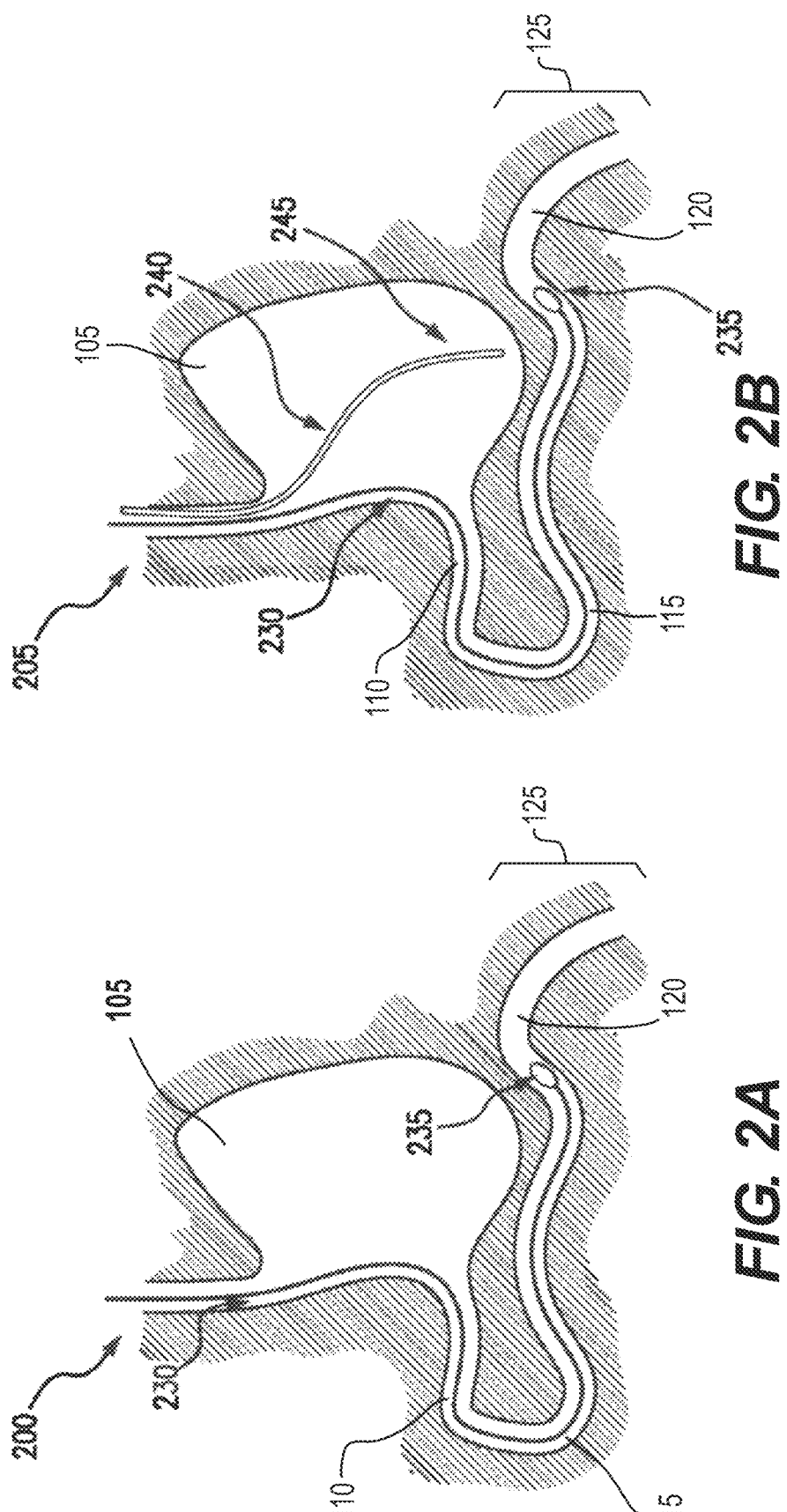
FIGS. 2A-2F illustrate an exemplary embodiment of a system and a process for creating an anastomosis, according to an aspect of the present disclosure.
Figures 2C, 2D:
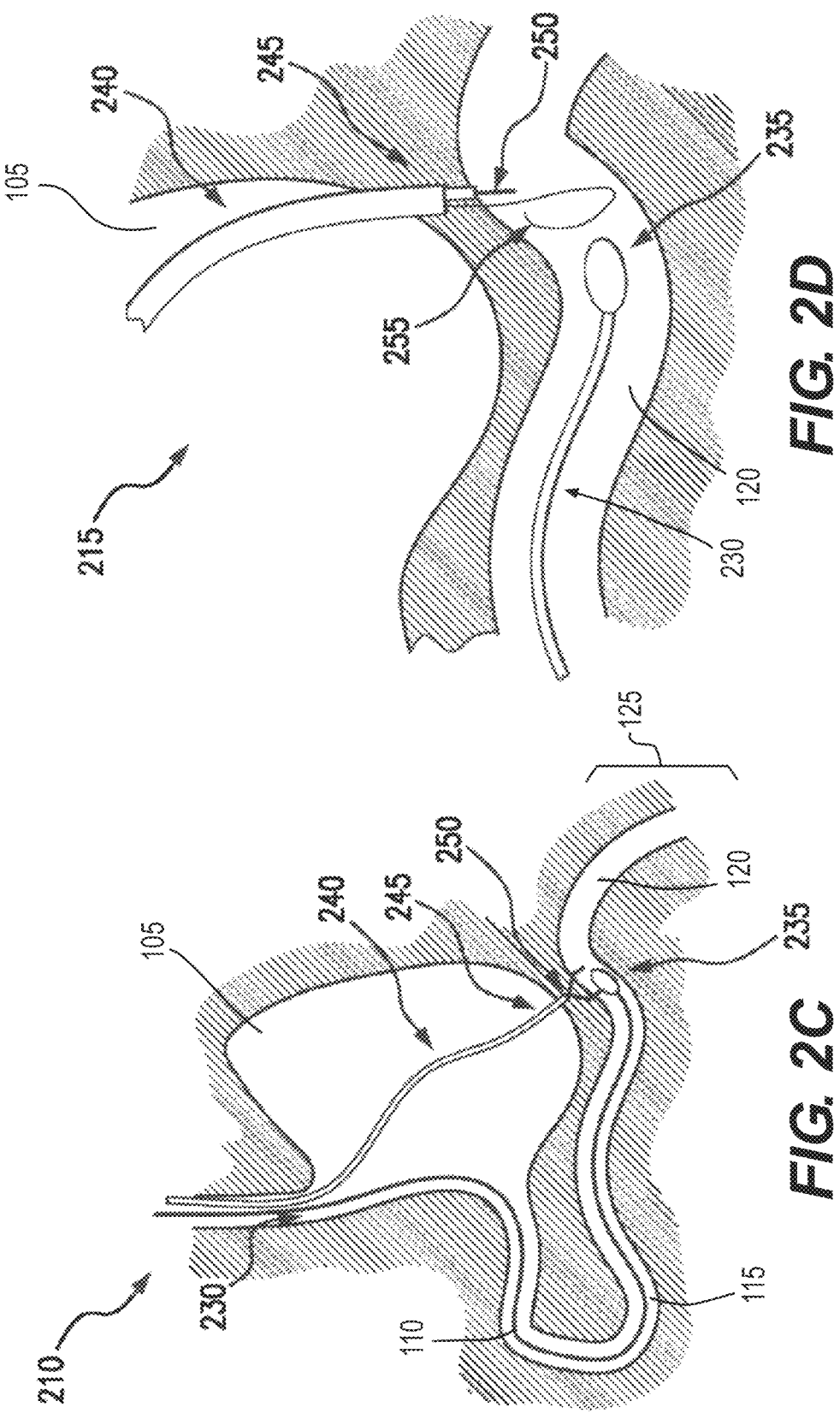

Once distal end 245 of endoscope 240 is in the proper position in stomach 105, a perforation or other incision is made in a lining of stomach 105 in step 210, as shown in FIG. 2C. A grasping mechanism, for example an end effector 250 at or extending from a distal end 245 of endoscope 240, and distal end 245 of endoscope 240 are advanced outside of stomach 105 after an incision is made in a wall of the stomach. A location of distal end 245 with respect to stomach 105 is determined by the medical professional by locating a location device at distal end 235 of nasocatheter 230, as will be described in detail herein. Once an outer wall of jejunum 120 is grasped by the grasping member, an incision or other opening may be made in jejunum 120, as will be described herein.

Figures 2E, 2F:
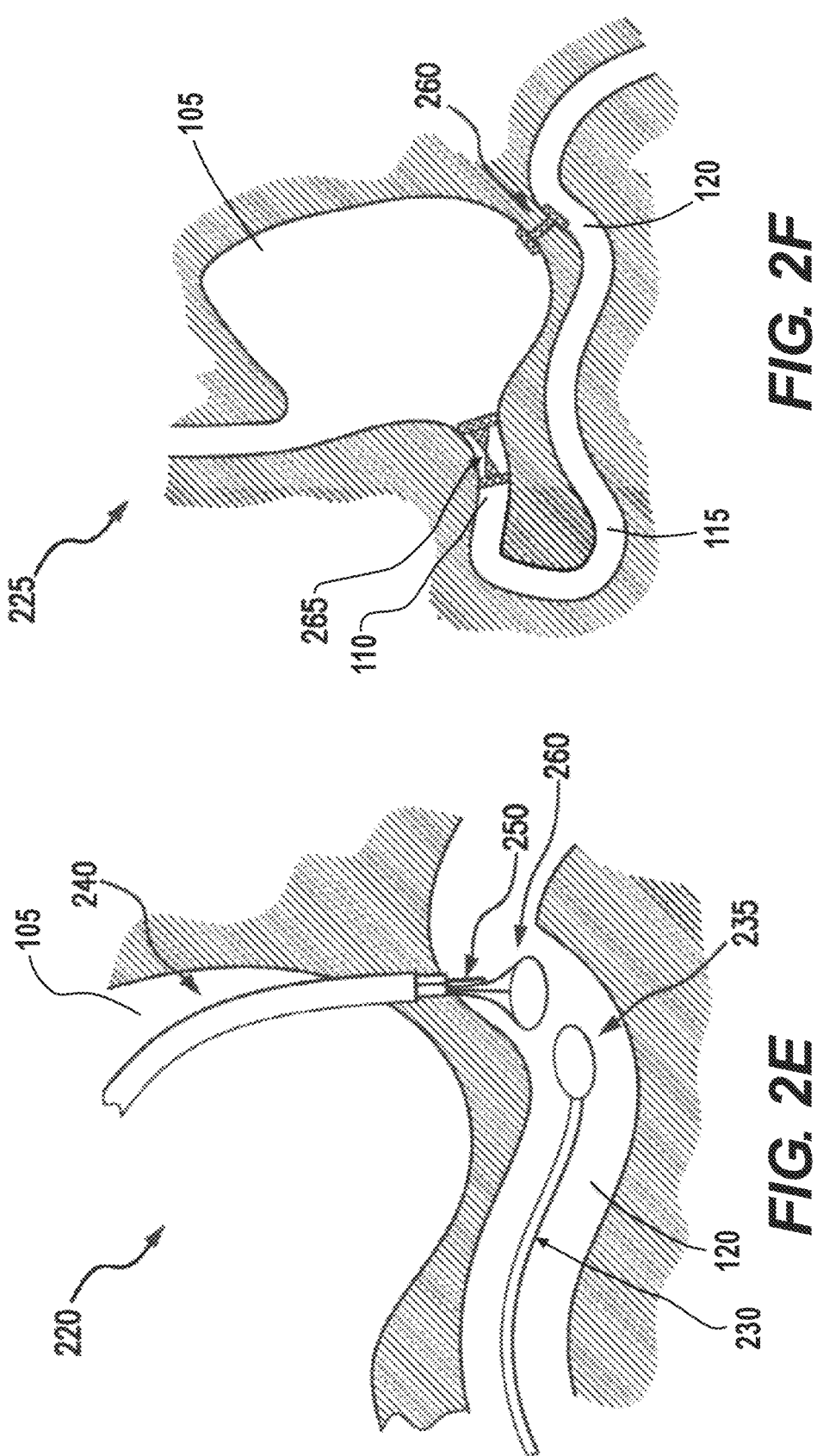

In step 215 shown in FIG. 2D, a perforation mechanism 250 may pierce jejunum 120 while maintaining the position of nasocatheter 230 in jejunum 120 via, e.g., an anchoring guidewire 255. It will be understood that the position of distal end 235 of nasocatheter 230 and, thus, the position of the incision in small bowel 125 may depend on the patient and/or on a medical procedure. As shown in FIG. 2E, an anastomosis stent 260 is deployed from endoscope 240 in step 220 to join the opening made in the wall of stomach 105 and the opening made in the wall of the jejunum 120, thereby creating a bypass of pylorus 110 and duodenum 115, e.g., a gastrojejunal anastomosis.

In FIG. 2F, a pyloric occlusion device 265 may be deployed at the pylorus to prevent a patient's stomach contents from traveling through pylorus 110 and redirecting this stomach content through anastomosis stent 260. Pyloric occlusion device 265 may be any configuration to prevent food, liquid, and/or nutrients from flowing from stomach 105 into duodenum 115. Rather, stomach contents may pass directly from stomach 105 to jejunum 120 via anastomosis stent 260, thereby limiting and/or preventing nutrients, food, and/or liquid from being taken up by the body in duodenum 110 (this procedure may include, but is not limited to, a gastroentral anastomosis procedure, a gastrojejunal anastomosis procedure, and/or a gastroduodenal anastomosis procedure). This may limit and/or prevent certain medical conditions such as weight gain and diabetes. It will be understood that the medical professional may later remove pyloric occlusion device 265 and/or anastomosis stent 260, thereby increasing absorption of food, liquid, and/or nutrients by stomach 105 and/or duodenum 115. While endoscopic procedures for placing an anastomosis device are described herein, additional procedural and device features for pyloric occlusion devices and anastomosis stents and stenting, which may be helpful, can be found in the complete disclosures of U.S. Pub. No. 2019/0298401, filed Mar. 22, 2019, published Oct. 3, 2019, and titled, "Systems and Methods For Performing Endoscopic Procedures," and U.S. Pub. No. 2019/0298559, filed Mar. 22, 2019, published Oct. 3, 2019, and titled, "Devices, Systems, and Methods For Pyloric Occlusion," each of which disclosures are incorporated herein by reference in their entireties.

Figure 3A:
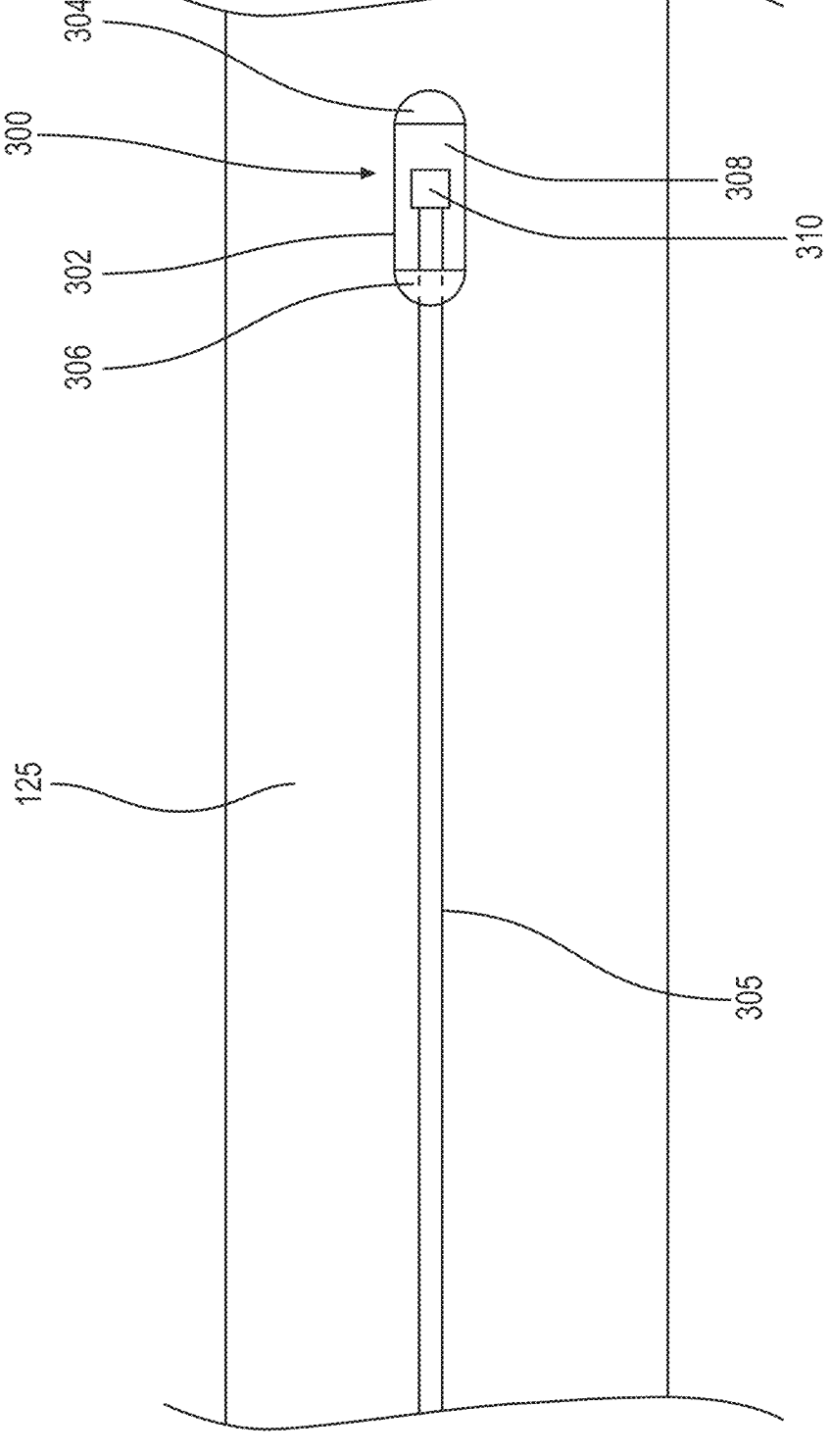
FIGS. 3A-3D are perspective views of examples of a catheter and a location device for use with the system of FIGS. 2A-2F, according to an aspect of the disclosure.
Figure 3B:
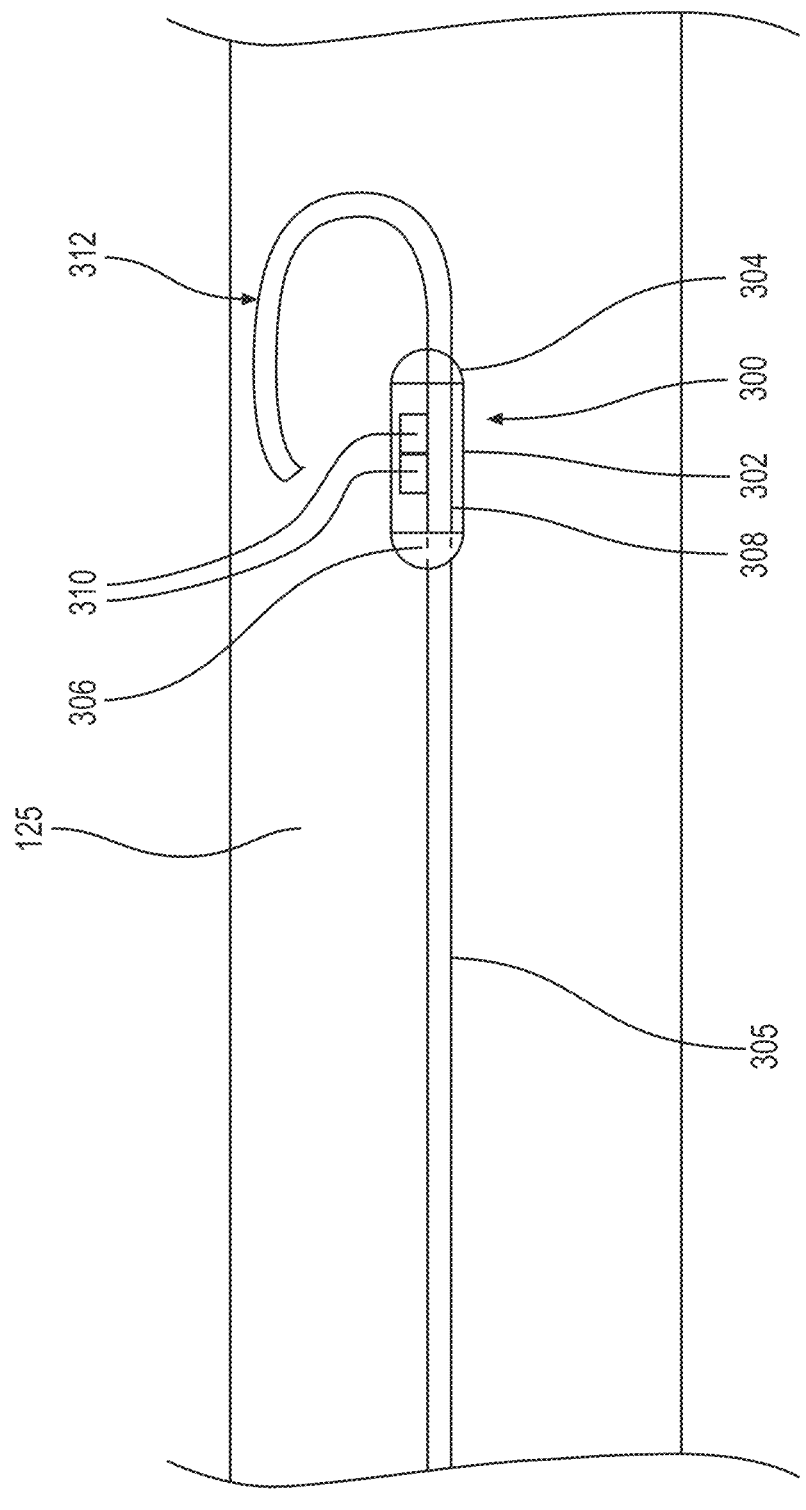

As described above, distal end 235 of nasocatheter 230 may be positioned in jejunum 120 to aid the medical personnel in determining a proper location to deploy the anastomosis stent. An example location device for locating a distal end of a nasocatheter is shown in FIG. 3A. For example, the distal end may include a location device 300 attached at its proximal end to a sheath, a guidewire, or a catheter 305. As used herein, the term "elongated member" or "elongate member," unless stated otherwise, may include any catheter (including a nasocatheter, oral catheter, anal catheter, or other endoscopic catheter), sheath, shaft, guidewire, wires, endoscope, or any member attached to a location device (with or without a lumen extending therethrough) including a location device 300 thereon. It will be understood that location device 300 may be placed proximal to the distalmost end of sheath, guidewire, or elongate member 305, as shown in FIG. 3B. For example, elongate member 305 may include a guidewire or the like to provide structural support to move elongate member 305 proximally and/or distally, or to allow a medical professional to place the guidewire in small bowel 125 and slide elongate member 305 along the guidewire. Location device 300 may be attached to an outer surface of elongate member 305 using an adhesive or the like, and may be positioned a distance from the distalmost end of elongate member 305, for example, a distance of approximately 15 cm. The elongate member 305 may be approximately 4 meters in length or less, e.g., approximately 3 meters, but is not limited to this length. Elongate member 305 may have a diameter of approximately 0.035 inches, or approximately 0.025 inches elongate member 305 without a lumen, or may have a diameter of approximately 7F, or approximately 5F for elongate member 305 including a lumen. The distance and diameter are not limited and may change according to a patient's size and/or a therapeutic procedure being performed by the medical personnel.

Elongate member 305 may also include a loop 312, as shown in FIG. 3B, in which a distal end of elongate member 305 is bent or curved and such that the distalmost end of elongate member 305 faces a generally proximal direction. Loop 312 may be formed after introducing elongate member 305 into the body by pushing elongate member 305 distally. For example, at least a portion of elongate member 305 may be flexible, or have a variable stiffness, causing a distal end of elongate member 305 to fold back on itself during a medical procedure, thereby forming loop 312 from a straight-line configuration. As elongate member 305 is moved proximally, loop 312 may approach the straight-line configuration. Loop 312 may provide a blunted end, which may reduce the chance of perforation of the bowel when maneuvering elongate member 305 and may increase the precision of locating location device 300. Loop 312 may alternatively be formed in or about a guidewire, and elongate member 305 may extend along the guidewire via a lumen, as will be described herein. It will be understood that conductive wires for conducting electricity may be disposed inside a lumen in elongate member 305 and/or located on an outer surface of elongate member 305. Alternatively, the conductive wires may be encapsulated within a wall of elongate member 305 and/or between walls of a multilayer elongate member 305.

According to the example shown in FIG. 3A, location device 300 may include one or more light emitting diodes (LEDs) 310. Location device 300 may include a sidewall 302, a distal end wall 304, and a proximal end wall 306. Location device 300 may be, e.g., a capsule, and may take any shape including, but not limited to, an ellipsoid, a cuboid, or a sphere. Sidewall 302 may be a single wall having a cylindrical shape, as shown in FIG. 3A, or sidewall 302 may include a plurality of sidewalls forming, for example, a rectangular prism. An internal space 308 may be formed between sidewall 302, distal end wall 304, and proximal end wall 306. Space 308 may include a fluid, atmospheric air, and/or an inert or other gas. For example, location device 300 may include an alternative light emitting feature in which electrodes are provided within and at opposite ends of internal space 308 and a gas, such as a neon gas, is disposed within internal space 308.

According to an example, LEDs 310 may be positioned within internal space 308. Each of LEDs 310 may be any shape, e.g., rectangular, but is not limited thereto. Additionally, or alternatively, a number of LEDs 310 may be arranged in any shape, including a triangular shape (e.g., three LEDs 310 angled 120 degrees relative to each adjacent LED 310) a cube (e.g., four LEDs 310 angled 90 degrees relative to each adjacent LED 310), and/or may form an inline orientation with each LED 310 facing a different direction. A light emitted from LEDs 310 may be emitted from internal space 308 of location device 300 via sidewall 302, which may be transparent or semitransparent. According to an example, one or both of distal end wall 304 or proximal end wall 306 may include or may be formed of an opaque or otherwise light attenuating material, which may focus the light emitted from LEDs 310 through sidewall 302 and which may assist a medical professional in locating location device 300. As will be described in detail herein, each diode from LEDs 310 may emit one or more wavelengths of light of visible light, as will be described herein. The number of LEDs 310 is not limited. As an example, a single red LED 310 and a single green LED 310 may be on a first side of elongate member 305, and a single red LED 310 and a single green LED 310 may be positioned on a circumferentially opposite side of sheath or guidewire 305. As another example, one or more red LEDs 310 may be on the first side of elongate member 305, and one or more green LEDs 310 may be on the circumferentially opposite side of elongate member 305. Alternatively, there may be one LED of each color, or, for example, two (2) to ten (10) or more LEDs 310 of each color. Alternatively or additionally, LEDs 310, and any LED described herein, may be arranged in multiple rows, e.g., two or more rows parallel or substantially parallel to a longitudinal axis of elongate member 305 and location device 300, and may be arranged around an entire circumference of elongate member 305, or may only extend about part of the circumference of elongate member 305.

Alternatively, location device 300 may include one or more LEDs 310 arranged on elongate member 305, as shown in FIG. 3B. FIG. 3B shows one array of two LEDs 310, and the colors of each of these LEDs 310 may be the same or different, e.g., one green LED 310 and one red LED 310. As further examples, LEDs 310 may be located in an array of 1 to 20 LEDs, or 4 to 6 rows of LEDs, with each row parallel to a longitudinal axis of elongate member 305 and location device 300. The rows may be arranged circumferentially about elongate member 305. Alternatively, LEDs 310 may be arranged on only one side of elongate member 305, for example, to focus the light emitting from LEDs 310 to only one side of location device 300. LEDs 310 may flash, e.g., may turn on and off, in a pattern. For example, LEDs 310 may flash at approximately 1 Hertz, with a duty cycle approximately 10-15% and a current of approximately 150 mA.

A covering, such as an electrically insulating heat shrink or a hardening substance such as glue, may be placed over sidewall 302, distal end wall 304, and proximal end wall 306, or may replace these walls entirely such that the covering covers all or part of LEDs 310. This covering is not limited to a location at only LEDs 310, and may extend in a distal and/or a proximal direction along elongate member 305 to ensure a sufficient adhesion of LEDs 310 to elongate member 305. The covering may be transparent or semi-transparent such that light from LEDs 310 may be transmitted therethrough.

Each LED 310 may emit a red light and/or a green light. Red light is absorbed relatively less by human tissue and therefore scatters, but is more easily viewed from a distance than green light due to its higher transmission through human tissue. Green light is absorbed relatively more by human tissue, resulting in lower transmission than red light. However, green light is more easily located than red light due to green light's decreased scattering within the body. Furthermore, a medical personnel's eyes and the image sensor of an endoscope (e.g., a CMOS image sensor or the like) are generally more sensitive to a wavelength of green light than a wavelength of red light, which may further improve determining the specific location of LEDs 310. For example, LEDs 310 (e.g., a first LED 310) may be controlled to emit the red light to determine a general area in which location device 300 is located, and LEDs 310 (e.g., a second LED 310) may emit the green light to more particularly locate the precise position of location device 300. Thus, the red light may be a coarse locator, or first adjustment, for identifying and positioning the medical device towards a desired location, and the green light may be a fine, or second adjustment, for identifying and positioning the medical device at the desired location. In some embodiments, the red light may be manually (or automatically) switched to a green light when the user has generally positioned the medical device as desired. In some embodiments, the red light and the green light may alternate at pre-selected intervals, so that the user may direct the medical device towards the desired location as the red and green lights alternate. Additionally, or alternatively, LEDs 310 may generate the red light and the green light at a same time, e.g., a first LED 310/light array may generate the red light, and a second LED 310/light array may generate the green light. It will be understood that LEDs 310 are not limited to these colored lights and may include other lights including, but not limited to, a white light.

With reference to FIG. 3A, a distal end of sheath, guidewire, or elongate member 305 may extend through an opening in proximal end wall 306, and the opening may subsequently be sealed around elongate member 305. Elongate member 305 may include a plurality of wires, e.g., two positive wires (one positive wire for each LED 310 anode terminal) and a common cathode return terminal wire, for conveying electrical energy from an electrical source (e.g., an electrical generator, a battery pack, or an equivalent energy source) at a proximal end of elongate member 305 to LEDs 310 and to provide independent control over each LED 310, which may improve efficiency of light transmission and may reduce heat from the light of LEDs 310 and any adverse effects associated with the heat on the body. For example, wires may be contained in a lumen or a layer of elongate member 305 extending from a proximal end to a distal end of elongate member 305 and/or wires may extend along an outer surface of elongate member 305 form the proximal end to the distal end. The wires may also be insulated with a biocompatible polymer and left uncovered or may be attached to a member having a greater stiffness. In this instance, the wires would form a "pill-on-a-string" and may be positioned at the desired location via peristalsis.

According to another example, location device 300 may include a disperser in the place of LED 310. Elongate member 305 may include a plastic or a glass diffused light pipe (elongate member 305 may be the diffused light pipe or the light pipe may replace the electrical wires conducting electricity to LEDs 310). Elongate member 305 may include reflective surfaces to advance a light to a distal end of elongate member 305. For example, the light may be coupled at a proximal end of elongate member 305 using a light source. Once the light reaches location device 300, the disperser may cause the light to disperse in one or more directions from location device 300, thereby illuminating location device 300. A medical professional may activate the light sources in any manner described herein.

Figure 3C:
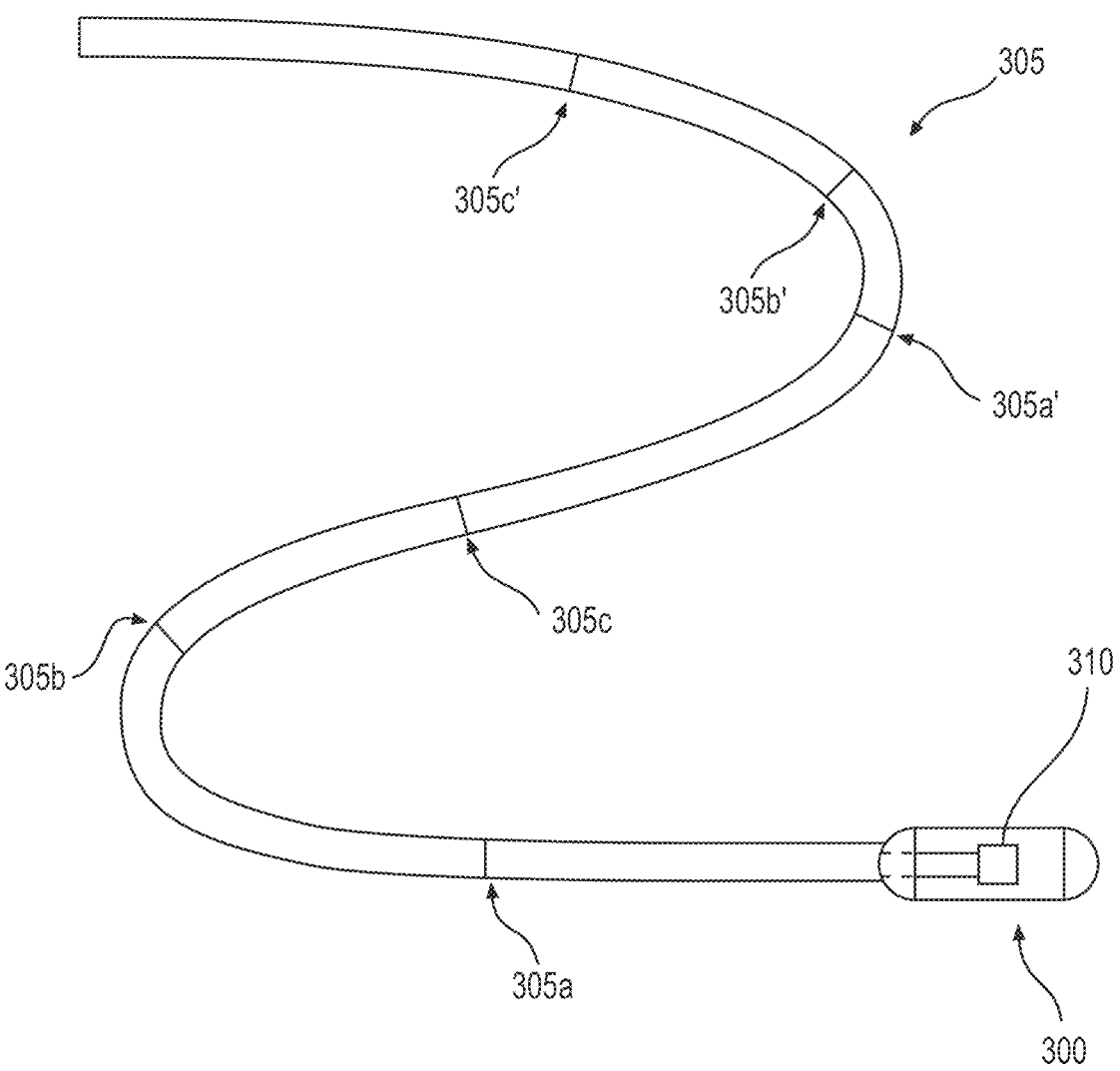
Figure 3D:
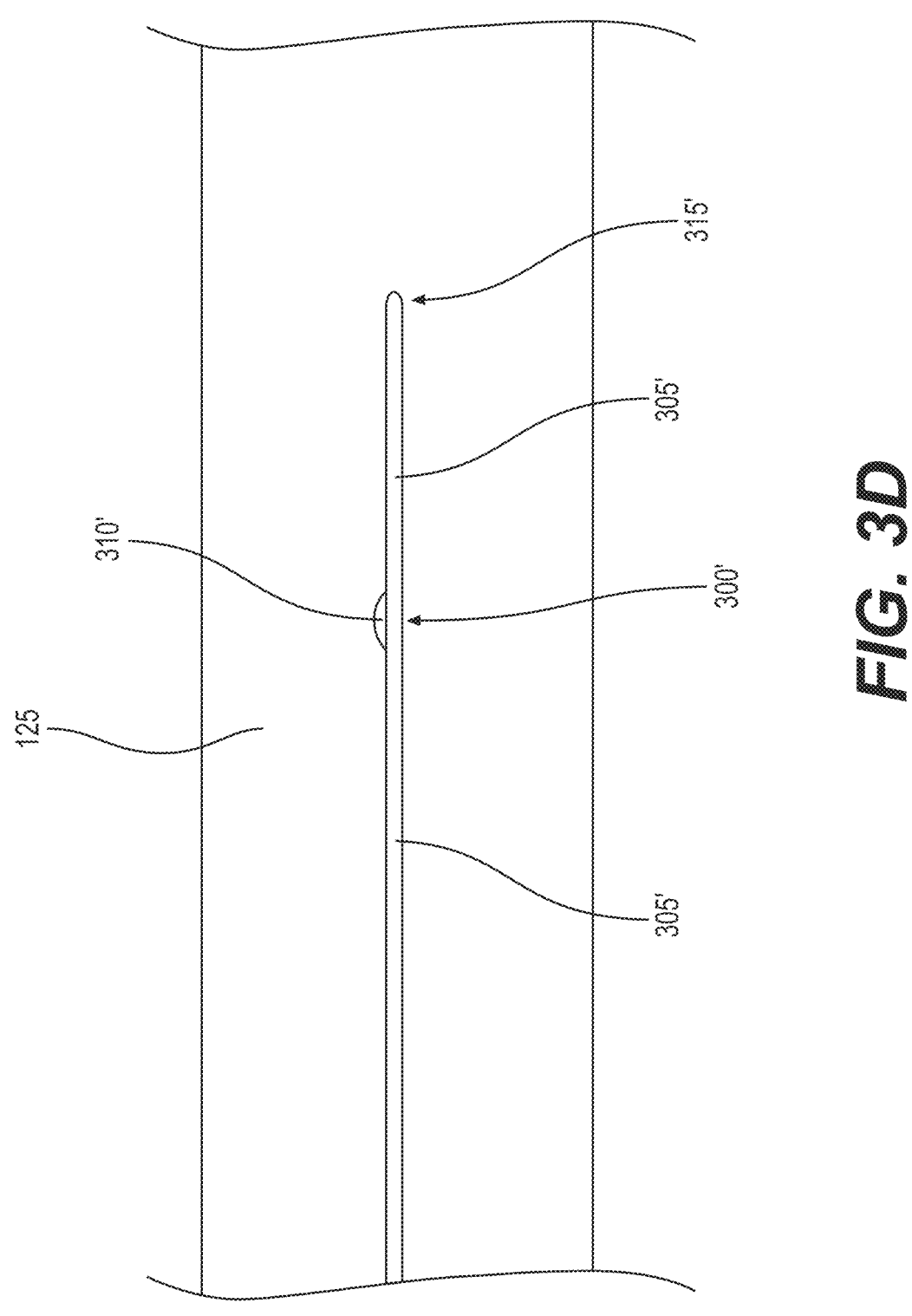

As shown in FIG. 3D, another example of a location device 300' on a guidewire, a sheath, or an elongate member 305' is shown. Location device 300', including one or more LEDs 310', may be positioned approximately 15 cm proximal to a distal tip 315' of guidewire 300'. Distal tip 315' may be rounded or may otherwise have a blunt end, which may minimize harm done to the esophageal pathway during insertion. Wires for carrying electricity from an electrical source to LEDs 310' may be disposed on or in guidewire 300', as described herein. elongate member 305' may have a diameter of approximately 0.035 inches, or approximately 0.025 inches. It will be understood that location device 300' may be disposed at any location along elongate member 305'. It will also be understood that guidewire 300' may be inserted into a patient's body and advanced to small bowel 125 in any manner described herein.

As shown in FIG. 3C, sheath, guidewire, or elongate member 305 may include markers, e.g., pylorus markers 305a, 305b, and 305c and teeth markers 305a', 305b', and 305c' to indicate a distance location device 300 has traveled when inserted into a patient. For example, a first pylorus marker 305a may be placed on elongate member 305 approximately 155 cm proximally from location device 300, a second pylorus marker 305b may be placed on elongate member 305 approximately 170 cm proximally from location device 300, and a third pylorus marker 305c may be placed approximately 185 cm proximally from location device 300. Additionally, or alternatively, a first teeth marker 305a' may be placed on elongate member 305 approximately 250 cm proximally from location device 300, a second teeth marker 305b' may be placed on elongate member 305 approximately 265 cm proximally from location device 300, and a third teeth marker 305c' may be placed approximately 280 cm proximally from location device 300. The markers may assist and/or indicate an approximate position of location device 300 with respect to an anatomy of the patient. For example, as will be described herein, location device 300 may be administered via the mouth, an esophageal pathway, and/or another percutaneous gastrointestinal access point such that when first teeth marker 305a' is aligned with the patient's teeth, the medical professional will understand that location device 300 has traveled approximately 250 cm into the patient. Similarly, when second teeth marker 305b' and third teeth marker 305c' are aligned with the patient's teeth, the medical professional will understand that location device 300 has traveled approximately 265 cm and 280 cm, respectively, into the patient. In some cases, however, elongate member 305 may become looped in stomach 105, and teeth markers 305a', 305b', and 305c may not provide as accurate distance results. Thus, the medical professional may determine a distance of location device 300 into small bowel 125 using pylorus markers 305a, 305b, and 305c using an image sensor on a distal end of endoscope 240. For example, when first pylorus marker 305a is aligned with pylorus 110, as determined using the image sensor, the medical professional may determine that location device 300 has extended approximately 155 cm into small bowel 125 from pylorus 110. Similarly, when second pylorus marker 305b and third pylorus marker 305c are aligned with pylorus 110, the medical professional may determine that location device 300 has extended approximately 170 cm and 185 cm, respectively, into small bowel 125 from pylorus 110.

Alternatively or additionally, elongate member 305 may be color coded such that an outer surface of elongate member 305 may include a first color between location device 300 and first pylorus marker 305a (or a position approximately 155 cm from location device 300), a second color on the outer surface between first pylorus marker 305a and second pylorus marker 305b (or a position approximately 170 cm from location device 300), a third color on the outer surface between second pylorus marker 305b and third pylorus marker 305c (or a position approximately 185 cm from location device 300), a fourth color on the outer surface from third pylorus marker 305c to first teeth marker 305a' (or a position approximately 250 cm from location device 300), and so on for all location markers on elongate member 305. It will be understood that regions that are not adjacent, e.g., a region between location device 300 and first pylorus marker 305a and a region between second pylorus marker 305b and third pylorus marker 305c, may be a same color.

Placement of the markers (and/or color transitions) is not limited to the locations described herein. For example, the markers may be placed along elongate member 305 based on physical characteristics of a patient, e.g., markers may be spread apart further along elongate member 305 for use in taller patients than for smaller patients, and/or based on the medical issue being treated, e.g., a morbidly obese patient may require markers spaced further apart along elongate member 305 to position location device 300 at a position more distal in jejunum 120 than for a patient having minor to moderate obesity.

It will be understood that pylorus markers 305*a*-305*c* and teeth markers 305*a'*-305*c'* may be any identifying element, e.g., a colored marking, a raised area of elongate member 305, a decal, text identifying a distance from location device 300, a series of circumferential stripes, or the like. Each of pylorus markers 305*a*-305*c* and teeth markers 305*a'*-305*c'* may include a plurality of markings, e.g., first pylorus marker 305*a* may include a plurality of the same color-coded markers in a same region of elongate member 305. In this manner, elongate member 305 may be suitable for use with patients of all sizes and/or for all medical procedures. Pylorus markers 305*a*-305*c* and teeth markers 305*a'*-305*c'* may also include characteristics to be identified by various medical imaging modalities. For example, pylorus markers 305*a*-305*c* and/or teeth markers 305*a'*-305*c'* may be radiopaque such that a location of each marker may be determined during the medical procedure using known medical imaging techniques. While elongate member 305 may have a strength suitable for pulling and/or pushing on elongate member 305, for example to move elongate member 305 when elongate member 305 is positioned within a patient, a guidewire may be used to position location device 300 within the body, and the guidewire and/or elongate member 305 may include these markers.

A method for positioning and operating location device 300 will now be described. An endoscopic procedure may be performed as discussed herein with reference to FIGS. 2A-2F. Before the procedure, location device 300 may be administered orally to a patient and swallowed. A proximal end of elongate member 305 may extend through the patient's nose. According to an example, location device 300 may advance along the gastrointestinal tract via peristalsis. In such an example (location device 300 swallowed and moved via peristalsis), location device 300 can be fed through nasal passages several hours before a proposed procedure. Alternatively, for elongate members 305 having relatively higher pushability, elongate member 305/location device 300 can be positioned endoscopically using an endoscope, e.g., endoscope 240.

To assist in proper location, the proposed procedure may begin once location device 300 is properly positioned within the gastrointestinal tract. For example, an imaging modality (e.g., an imaging device and/or a device to locate radiopaque devices) may be used to determine when pylorus markers 305*a*-305*c* are properly positioned at the pylorus. Alternatively, or additionally, the procedure may begin when teeth markers 305*a'*-305*c'* are properly positioned at the patient's mouth/teeth. The proper location of these markers may indicate to the medical professional that location device 300 is positioned at a proper location within jejunum 120. Alternatively, for elongate members 305 having greater pushability, elongate member 305 may be pushed until these markers are properly positioned, e.g., pylorus markers 305*a*-305*c* are positioned at the pylorus and/or teeth markers 305*a'*-305*c'* are positioned at the mouth, etc.

Elongate member 305 may be connected to an electrical source before, during, or after administering location device 300 to the patient. LEDs 310 may be activated at any point during the procedure. Alternatively, LEDs 310 may be activated when location device 300 has been advanced a certain distance into the patient, as indicated by one or more of markers 305*a*-305*c*. A medical professional may create an incision in a wall of stomach 105, such as in the antrum of stomach 105, and advance endoscope 240 through the incision. Subsequently, the medical professional may visualize the peritoneal cavity using a camera or other imaging device at distal end 245 of endoscope 240 to determine a position of location device 300 in jejunum 120. For example, a medical professional viewing an image of the peritoneal cavity, e.g., on a monitor associated with the camera of endoscope 240, may determine the position of location device 300 within jejunum 120 based on the location of light from LEDs 310 transmitted through a wall of jejunum 120. Location device 300 may provide the medical professional with a proper location for creating a perforation or an incision in a wall of jejunum 120 in steps 215 and 220 described herein. In this manner, the anastomosis device may be properly positioned. Alternatively, the medical professional may visualize location device 300 through both the wall of jejunum 120 and the wall of stomach 105, which may assist the medical professional in determining where to make an incision in both the wall of stomach 105 and an incision in the wall of stomach 105.

LEDs 310 may be activated according to a pattern. For example, one or more red LEDs 310 may be activated before or after location device 300 is orally administered and may be continuously turned on or may pulse. The medical professional may determine when the red light is located by the camera at distal end 245 of endoscope 240. The medical professional may then deactivate the red light and may activate the green light. It will be understood that the green light may also be continuously turned on or may pulse. Further, activation of the green light and deactivation of the red light may be automatically performed by a controller associated with the camera. After the green light is activated, the medical professional may further manipulate distal end 245 of endoscope 240 to position end effector 250 in a proper location for creating an incision in jejunum 120. Alternative embodiments may include activating both the red light and the green light at the beginning of the procedure and/or pulsing one or both of the lights during the procedure, and/or deactivating the red light once location device 300 is located by the camera. One or more white lights may also be activated through the procedure, which may assist the medical professional to better locate location device 300 once an incision is made in one or more of stomach 105 and jejunum 120.

Figure 4A:
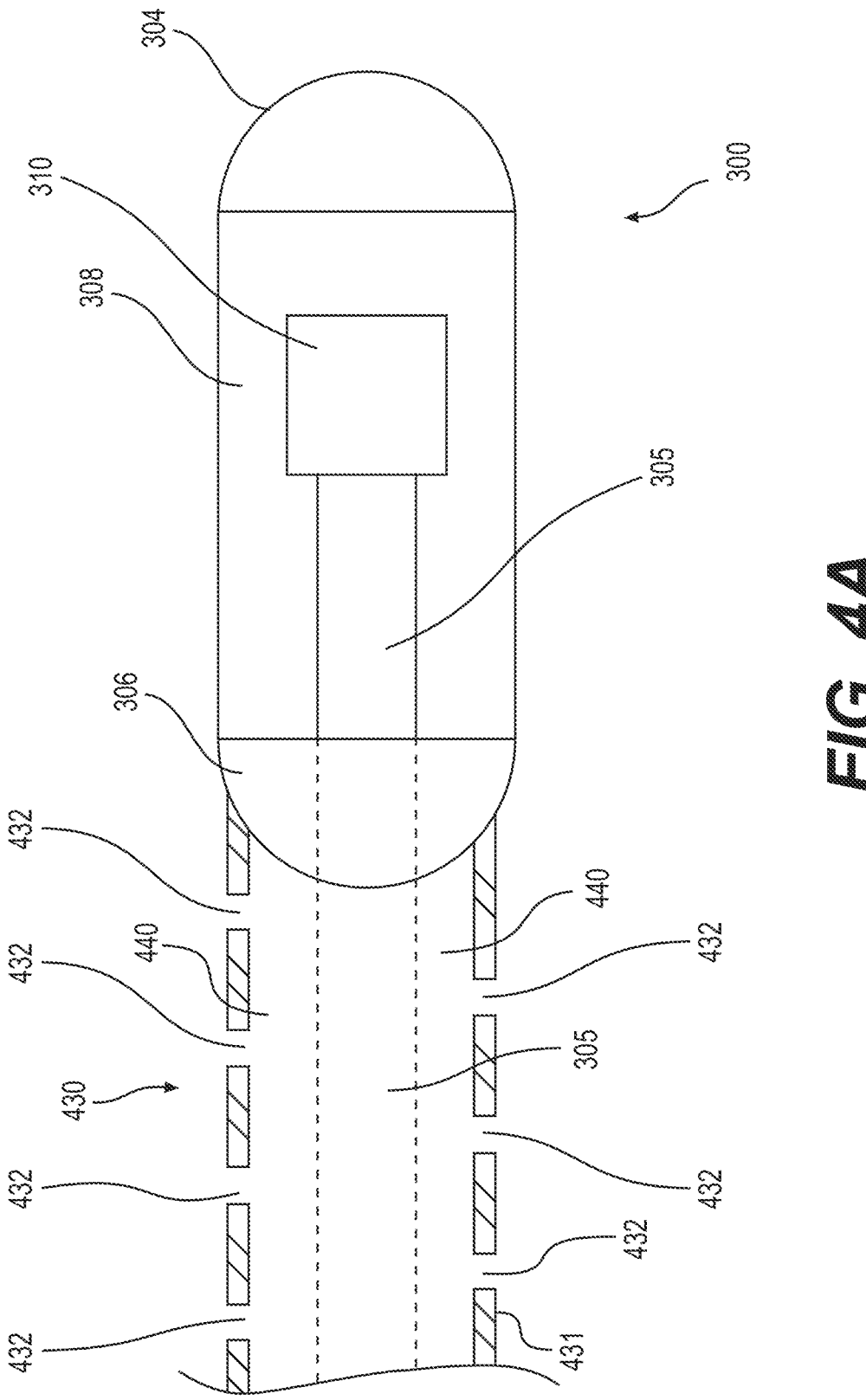
FIGS. 4A and 4B are perspective views of another example of an elongate member and a location device for use with the system of FIGS. 2A-2F, according to an aspect of the disclosure.
Figure 4B:
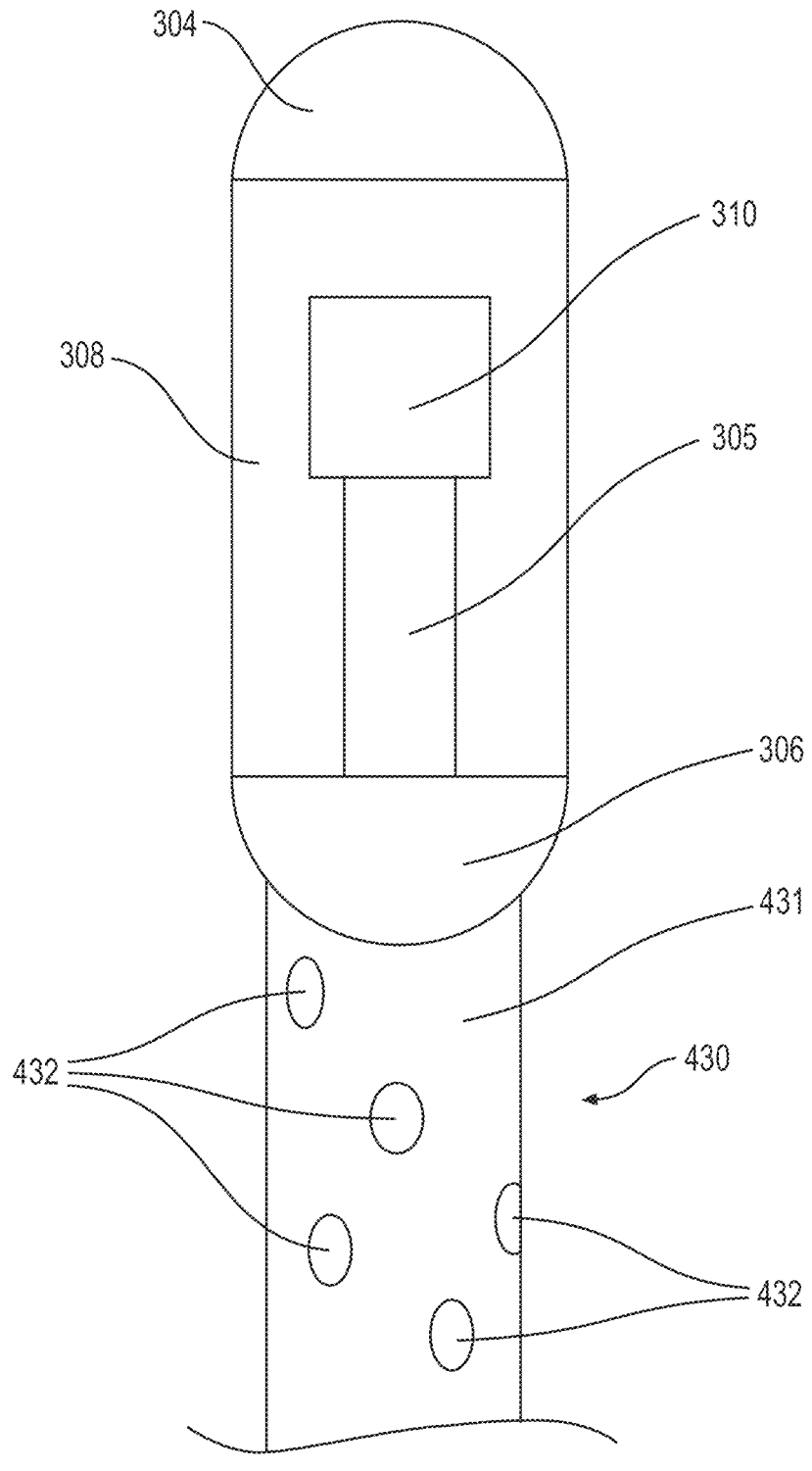

A nasocatheter 430 (a nasocatheter may include any catheter, sheath, or wire described herein) according to another example is shown in FIGS. 4A and 4B. According to an example, nasocatheter 430 may include a lumen 440 extending from a proximal end and may include a location device, such as location device 300, attached to a distal end thereof. For example, an outer sheath/tube 431 of nasocatheter 430 may define lumen 440. Lumen 440 may contain elongate member 305 described in connection with FIGS. 3A-3C. Sheath 431, however, may include the markers for determining distance. Outer sheath 431 may include a material having a sufficient stiffness to be maneuvered within the patient's body, e.g., to be pushed and pulled, without relying on bodily functions, such as peristalsis, to move nasocatheter 430 to a target location in jejunum 120. Outer sheath 431 may include holes 432, which may fluidly connect lumen 440 and an interior of a gastrointestinal pathway when nasocatheter 430 is inserted into a patient's body. Alternatively, holes 432 may be formed directly in a wall of elongate member 305, allowing fluid to pass within a central lumen of elongate member 305 (e.g., fluid may pass adjacent coated electrical wires). Holes 432 may be provided only at a distal end of sheath 431, and/or holes 432 may also be placed along an intermediate and/or a proximal length of nasocatheter 430. Holes 432 may be placed along a substantially same circumferential side of sheath 431 and/or may be placed around a circumference of sheath 431 at multiple locations along a length of sheath 431. Holes may have a diameter of approximately 0.020 inches to 0.040 inches, or approximately 0.025 inches to 0.030 inches. Holes 432 may assist in venting the gastrointestinal pathway, e.g., stomach 105 and/or small bowel 125, thereby releasing insufflation and/or naturally occurring gases from the gastrointestinal pathway. These gases may cause walls of stomach 105 and/or small bowel 125 (including jejunum 120) to expand, which may increase the distance light from LEDs 310 must travel from location device 300 to a sidewall of jejunum 120 and which may decrease the amount of light that passes from jejunum 120 into the peritoneal cavity and therefore be visible to the endoscope camera. This increased distance may create difficulties in locating a position of location device 300 in jejunum 120 from the peritoneal cavity. Since holes 432 may vent gases introduced into, and/or produced by, stomach 105 and/or small bowel 125, the expansion of the gastrointestinal walls may be reduced and visualization of light in the peritoneal cavity and/or stomach 105 from location device 300 positioned in jejunum 120 may be improved. It will be understood that a vacuum may be attached to a proximal end of lumen 440 to actively remove gases and/or a containment device may be attached to the proximal end of the lumen to contain gas removed from the gastrointestinal pathway.

A method for positioning and operating nasocatheter 430 will now be described. Nasocatheter 430 may be introduced to the body in any manner described herein. For example, nasocatheter 430 may be introduced via the mouth or the nose and may be advanced into the small bowel by manipulating and/or pushing on a proximal end of nasocatheter 430, or via peristalsis. As nasocatheter 430 moves along the gastrointestinal pathway, gases may actively or passively enter holes 432 and travel proximally along lumen 440 to a proximal outlet. For example, a vacuum or other pump may be connected to lumen 440 at a proximal end of nasocatheter 430, and the vacuum may actively aspirate gases from the gastrointestinal pathway. Alternatively, these gases may travel passively along to the proximal outlet of lumen 440. For example, a buildup of gases in the gastrointestinal pathway may result in a pressure increase greater than an atmospheric pressure. The pressure differential between the gastrointestinal pathway and the atmosphere surrounding an outside of a patient's body may allow these gases to flow into holes 432, along lumen 440, and out the proximal opening of lumen 440. It will be understood that a containment device may be attached to the proximal opening of lumen 440 to prevent gases from the body to be released into a procedure room. It will also be understood that gases may be continuously removed during the anastomosis procedure.

Figure 5:
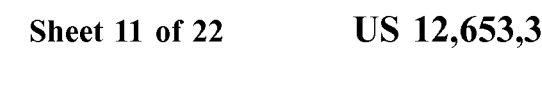
FIG. 5 is a perspective view of another example of an elongate member and a location device for use with the system of FIGS. 2A-2F, according to an aspect of the disclosure.

According to another example, a location device 500 may be attached to a catheter or a sheath 502 (sheath 502 may include any catheter or nasocatheter described herein), as shown in FIG. 5. Sheath 502 may include a guidewire lumen 504 through which a guidewire 505 may extend, allowing sheath 502 to travel along guidewire 505. Location device 500 may be positioned at a distal end of sheath 502. For example, location device 500 may be disposed on an outer surface of sheath 502, may protrude from an outer surface of sheath 502 as shown in FIG. 5, and/or may be provided in a separate tube attached to sheath 502. Alternatively, location device 500 may include a capsule, e.g., such as location device 300, provided at a distal end of sheath 502, and guidewire 505 may extend through a lumen in a center of the capsule to allow sheath 502 to slide along guidewire 505. According to an example, location device 500 may be removably attached to sheath 502. In this manner, different location devices 500, e.g., location devices 500 including different numbers of LEDs 510 and/or different colored LEDs 510, may be interchanged according to a procedure to be performed and/or a size or an anatomy of a patient. The increased rigidity of sheath 502, and its trackability over guidewire 505, may improve movement and operability of location device 500, thereby improving medical procedures. Alternatively, location device 500 may be pulled along an outer surface of the endoscope or through a lumen of the endoscope by an end effector, e.g., a pair of forceps, and into small bowel 125.

A method for introducing location device 500 will now be described. Guidewire 505 may be introduced via a natural orifice, e.g., a mouth, and advanced along the gastrointestinal system. Sheath 502 is subsequently inserted via the natural orifice by placing sheath 502 around guidewire 505 via guidewire lumen 504. Sheath 502 may be advanced along the gastrointestinal system in any manner described herein. Further, LEDs 510 may be activated in any manner described herein.

Figure 6:
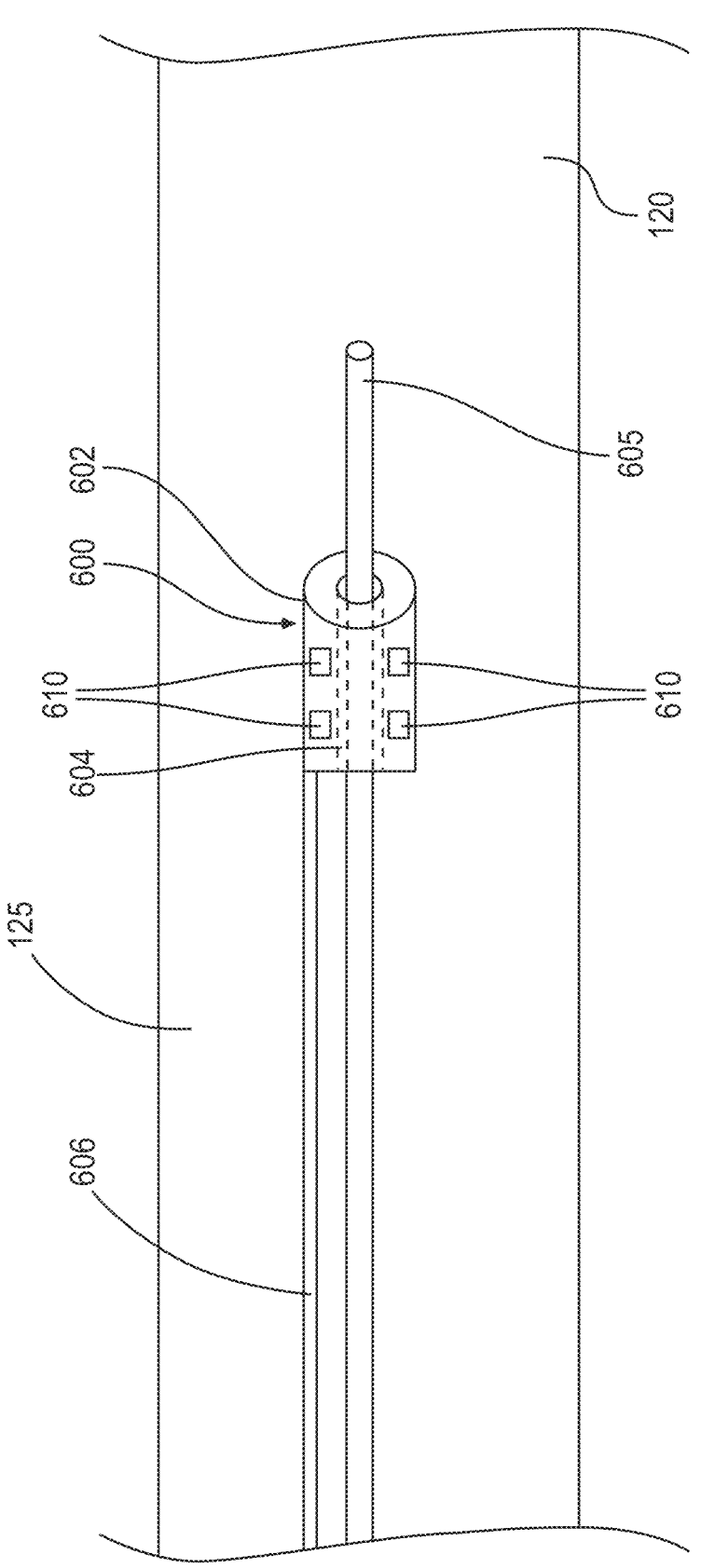
FIG. 6 is a perspective view of another example of an elongate member and a location device for use with the system of FIGS. 2A-2F, according to an aspect of the disclosure.

According to another example, a location device 600 may be attached at a distal end of a sheath 602 (sheath may include any catheter or nasocatheter described herein) having a central lumen 604. Sheath 602 may be shorter than other catheters described herein and sized to support LEDs 610, as shown in FIG. 6. For example, sheath 602 may be only long enough to support LEDs 610 and may be approximately 20 cm in length, approximately 10 cm in length, or approximately 5 cm in length. A pushing member 606 may be attached to a proximal end of sheath 602 to move sheath 602 along a guidewire 605. The reduced size of sheath 602 may improve maneuverability of sheath 602, pushing member 606, and guidewire 605, thereby allowing location device 600 to travel a tortuous path within the patient and/or to navigate a blockage or narrowing within the gastrointestinal pathway. Additionally, this may allow rapid exchange of location device 600 from guidewire 605, which may allow a single medical professional to manipulate guidewire 605 and location device 600. Pushing member 606 may be a wire suitable for use in a medical procedure and may include any material sufficient for such use. Pushing member 606 may have a stiffness suitable to receive and move location device 600 along guidewire 605. It will be understood that electrical wires may be supported by pushing member 606 such that LEDs 610 may receive power.

Location device 600 may be deployed in any manner described herein. For example, guidewire 605 may be introduced as described with respect to guidewire 605. Subsequently, sheath 602 may be placed over guidewire 605 via guidewire lumen 604. Pushing member 606 may then advance sheath 602 along guidewire 605 (via force applied at the proximal end of pushing member 606). LEDs 610 may be activated in any manner described herein such that the medical professional may locate location device 600 using the endoscope camera located in stomach 105.

Figure 7:
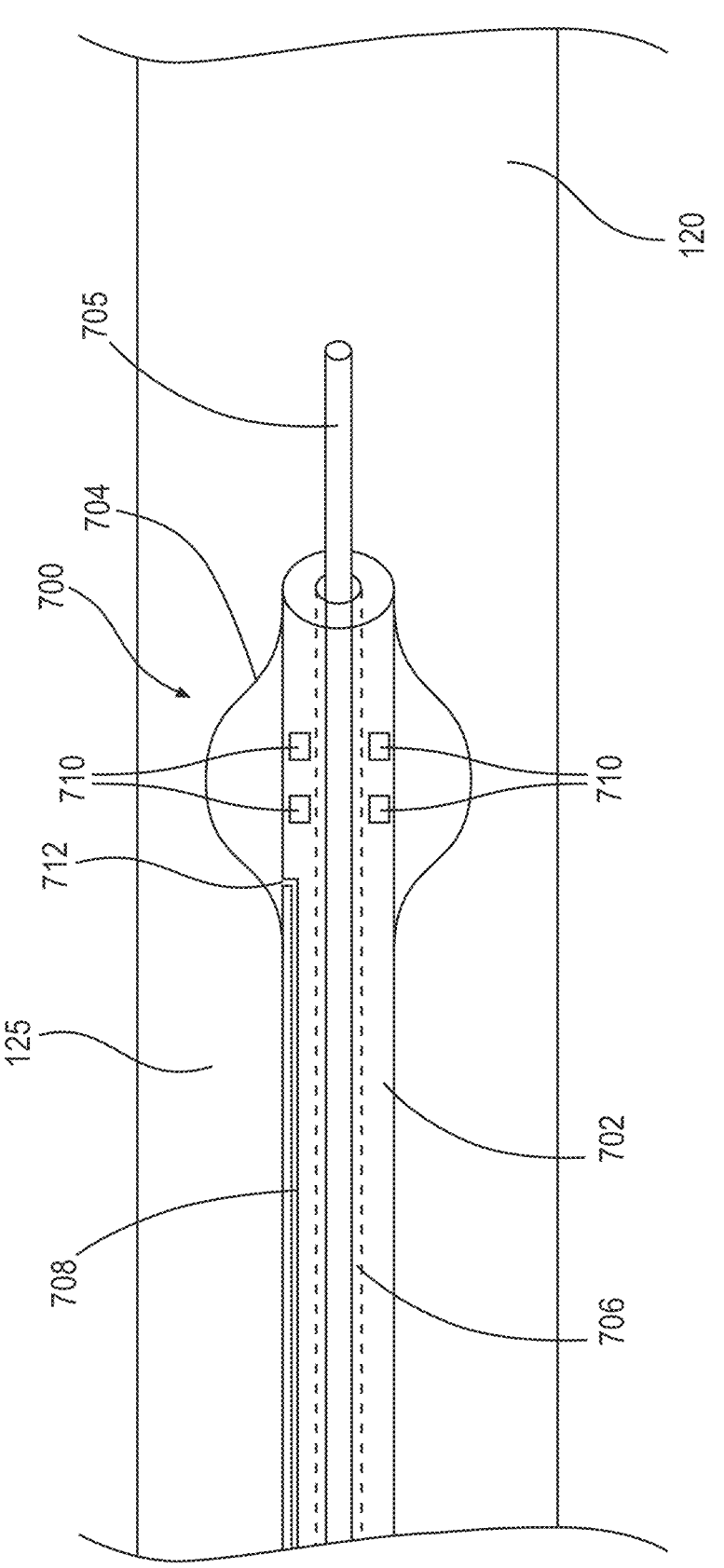
FIG. 7 is a perspective view of another example of an elongate member and a location device for use with the system of FIGS. 2A-2F, according to an aspect of the disclosure.

According to another example, location device 700 may be attached to and/or may surround a distal end of a sheath 702 (sheath may include any catheter or nasocatheter described herein). Location device 700 may include an expandable balloon 704 which may surround LEDs 710, as shown in FIG. 7. Balloon 704 may include a transparent or a semi-transparent material (e.g., polyethylene terephthalate (PET), polyethylene, polyamide copolymers (PEBA) latex, or the like) such that light from LEDs 710 may be transmitted through balloon 704 to a wall of jejunum 120. LEDs 710 may be any number and/or any color, and may be arranged on sheath 702 in any manner described in any of the embodiments herein. Sheath 702 may include a central lumen 706 which may receive a guidewire 705 and which may allow sheath 702 to slide proximally and distally over guidewire 705 as described herein. A fluid lumen 708 (shown in solid line) may extend through sheath 702 from a proximal end of sheath 702 to an outlet 712 in fluid communication with an interior of balloon 704. Lumen 708 may allow a fluid to be transmitted therethrough to inflate balloon 704. For example, a fluid containment device may be attached to the proximal end of fluid lumen 708, and the fluid may be introduced or removed from balloon 704 via fluid lumen 708.

A method of deploying location device 700 will now be described. Location device 700, including balloon 704, may be advanced to a target location according to any of the methods described herein. Balloon 704 is then inflated. Inflation of balloon 704 may cause balloon 704 to contact a wall of jejunum 120, thereby fixing a position of balloon 704 in jejunum 120. Contact between balloon 704 and the wall of jejunum 120 may eliminate air and/or fluid gaps between location device 700 and the wall of jejunum 120, which may increase light transmittance from LEDs 710 to and/or through the wall of jejunum 120 and may improve visualization of location device 700. It will be understood that LEDs 710 may include different colored lights as described herein, e.g., red and/or green lights, and the different colored lights may be activated in various patterns in any manner described herein. Once location device 700 is located by the medical professional and an incision is made in the wall of jejunum 120, balloon 704 may be deflated and sheath 700 may be removed from the body.

Figure 8A:
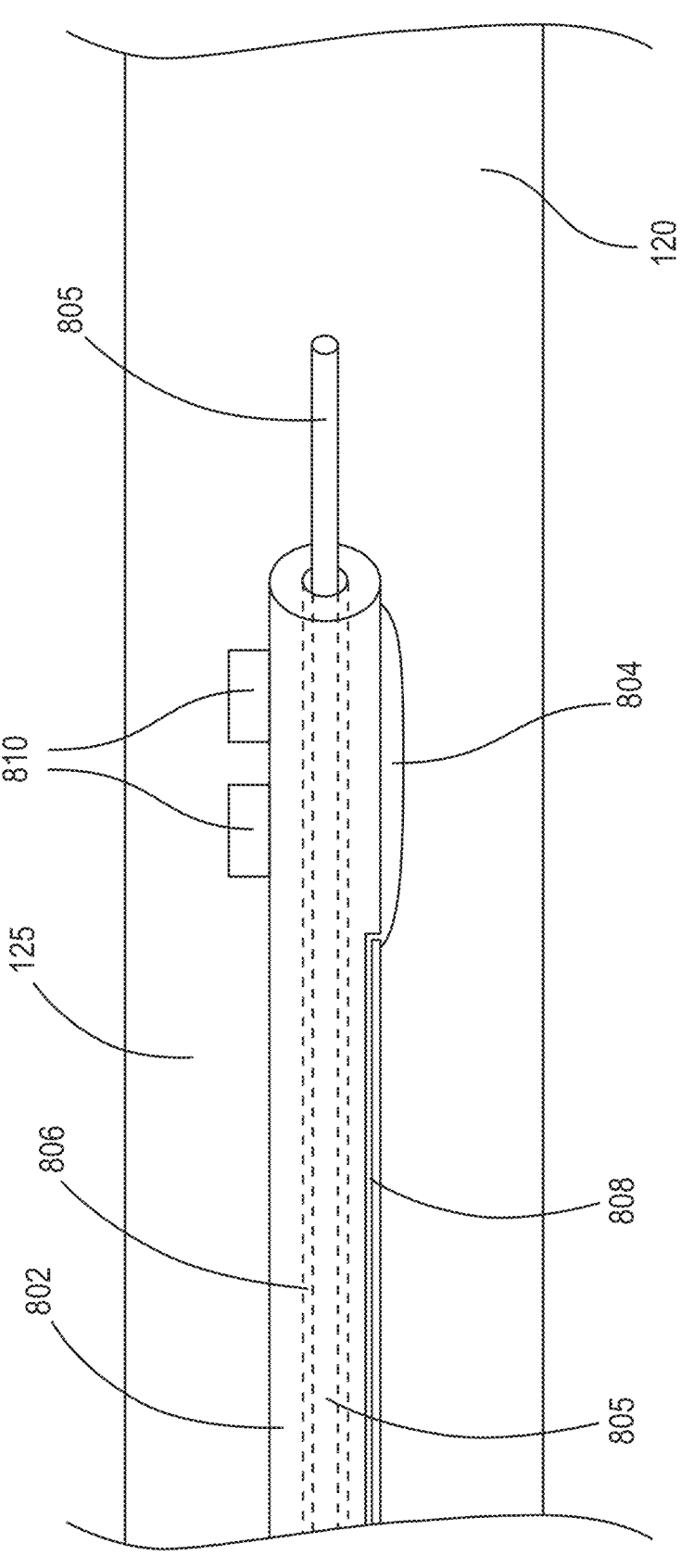
FIGS. 8A and 8B are perspective views of another example of an elongate member and a location device for use with the system of FIGS. 2A-2F, according to an aspect of the disclosure.
Figure 8B:
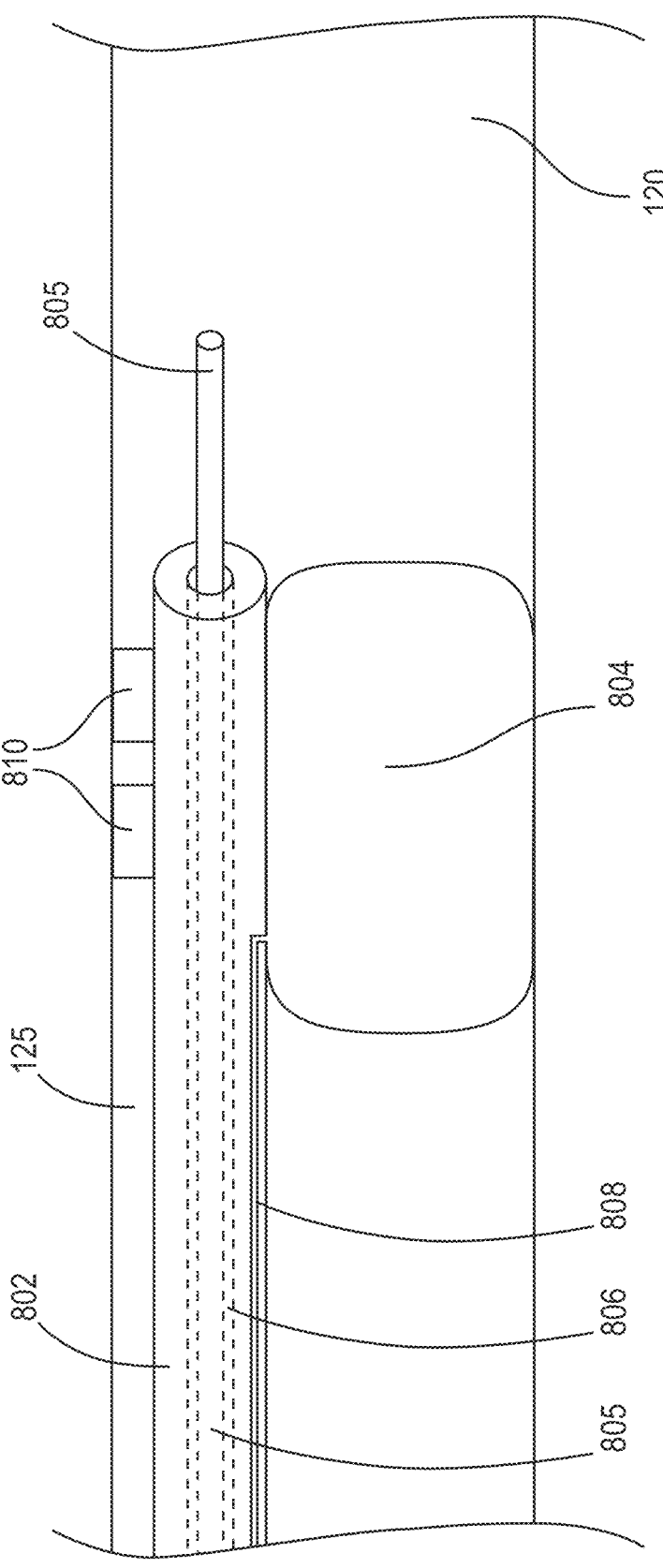

FIGS. 8A and 8B illustrate another example of a location device 800. Location device 800 may include a balloon 804 on a first side of a distal end of a sheath 802 (sheath 802 may include any catheter or nasocatheter described herein) and LEDs 810 on a circumferentially opposite side of sheath 802 from balloon 804. Balloon 804 may extend around only a portion of a circumference of sheath 802. The position of LEDs 810 is not limited thereto, and may extend about a circumference of sheath 802 to increase visibility of location device 800. Sheath 802 may include a central lumen 806 and may be advanced over a guidewire 805 (within lumen 806) to position location device 800 adjacent a wall of jejunum 120. Balloon 804 may be inflated using a fluid lumen 808 (shown in solid line) as shown in FIG. 8B, like fluid lumen 708 of sheath 702. For example, fluid lumen 808 may be connected at a proximal end to a fluid containment device for introducing or removing inflation fluid. Inflating balloon 804 may cause a side of balloon 804, opposite sheath 802, to contact a all of jejunum 120 and force the distal end of sheath 802 toward an opposing wall of jejunum 1290. Inflation presses or urges LEDs 810 against the wall of jejunum 800, which may eliminate air and/or fluid gaps between location device 800 and the wall of jejunum 120. This, in turn, may increase light transmittance from LEDs 810 to and/or through the wall of jejunum 120 and improves visualization of location device 800 by the imaging device in stomach 105. Location device 800 may be deployed similar to location device 700.

Figure 9:
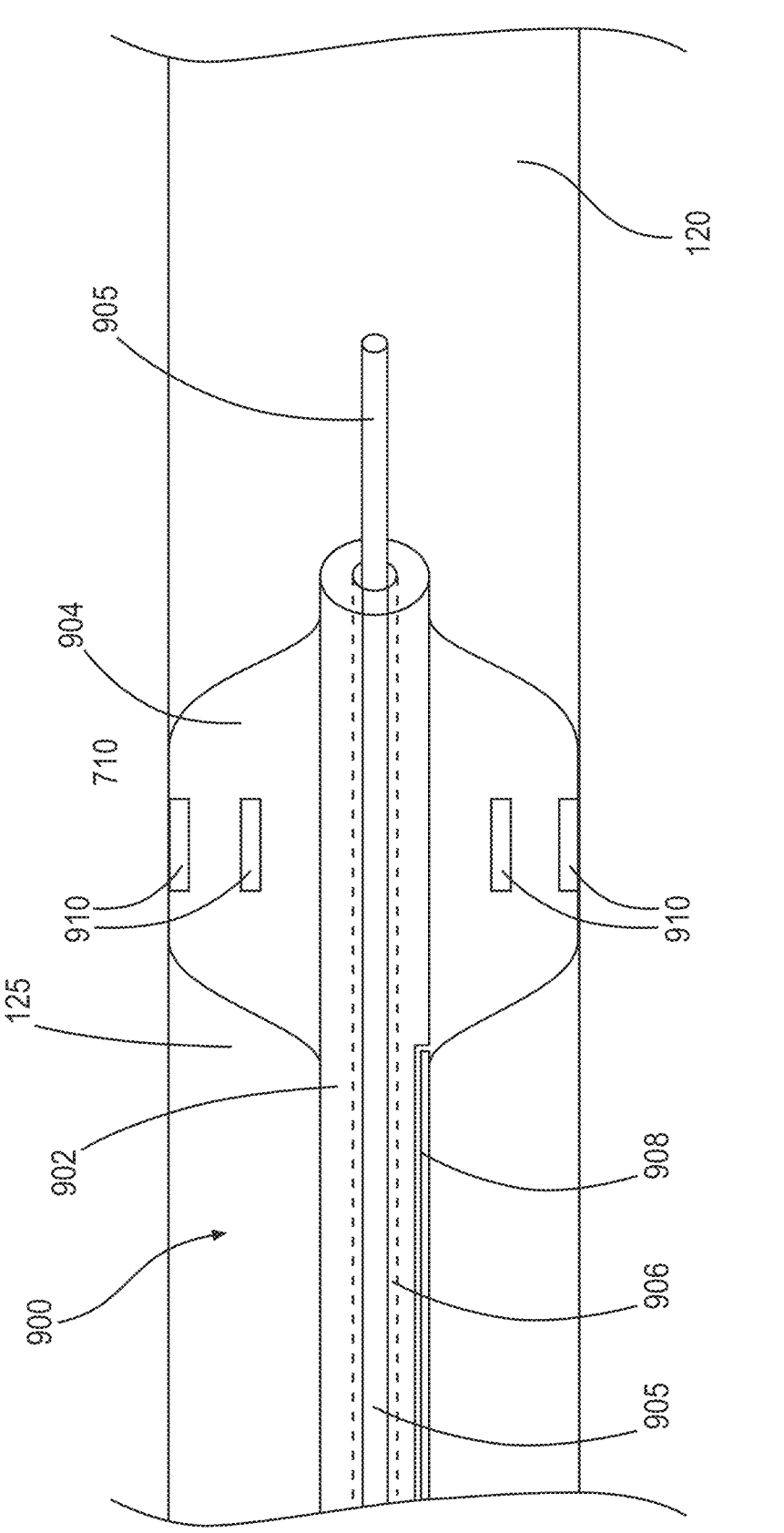
FIG. 9 is a perspective view of another example of an elongate member and a location device for use with the system of FIGS. 2A-2F, according to an aspect of the disclosure.

Another example of a location device 900 is illustrated in FIG. 9. Similar to location devices 700 and 800, location device 900 may include a balloon 904 on a distal end of a sheath 902 (sheath may include any catheter or nasocatheter described herein) and which may be inflated to position LEDs 910 against a wall of jejunum 120. Balloon 904 may surround all of distal end of sheath 902. As with location devices 700 and 800, sheath 902 may include a central lumen 906. The configuration of sheath 902 may allow sheath 902 to be advanced along a guidewire 905 (positioned in lumen 906) to a target site within jejunum 120. Once location device 900 is positioned at the target site, balloon 904 may be inflated in any manner described herein, such as using a fluid lumen 908 or the like attached at a proximal end to a containment device including an inflation fluid. LEDs 910 may be disposed on an outer surface of balloon 904. Wires (not shown) providing current/power to LEDs 910 may extend through sheath 902 and into the interior of balloon 904, or along a surface of balloon 904, to electrically connect to LEDs 910. Inflation of balloon 904 may press or urge LEDs 910 against the wall of jejunum 120. LEDs 910 may alternate between red and green lights around a circumference of balloon 904, or LEDs 910 may include an array of red lights circumferentially disposed about balloon 904 adjacent an array of green lights similarly disposed about the circumference of balloon 904. LEDs 910 may be centered along a longitudinal axis of balloon 904 and may be equally spaced about an outer circumference of balloon 904. Alternatively, LEDs 910 may be positioned on an outer surface of balloon 904 on circumferentially opposite sides balloon 904, which may improve visualization of LEDs 910. It will be understood that red and green lights of LEDs 910 may be actuated independently or together in any manner described herein.

Figure 10A:
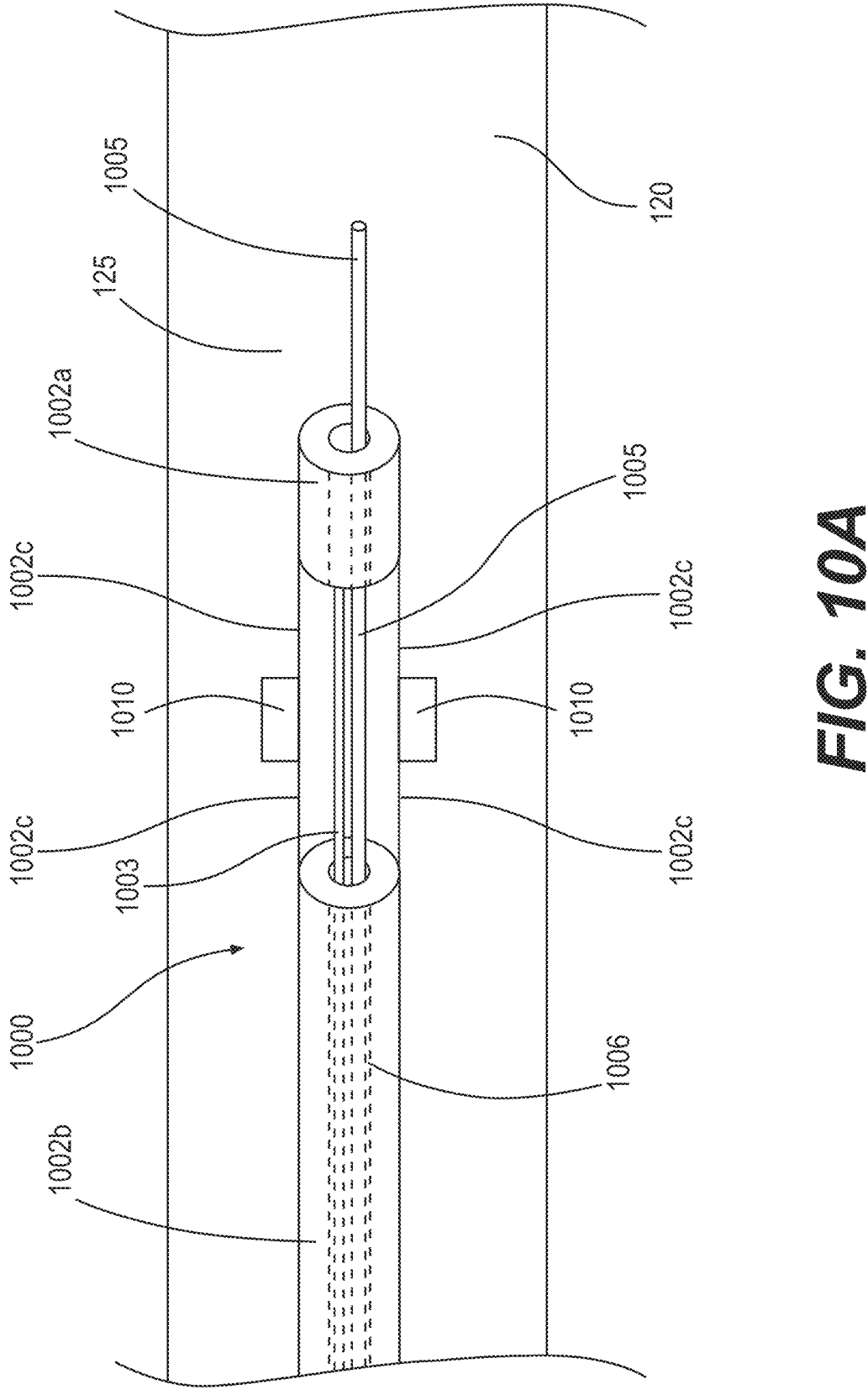
FIGS. 10A and 10B are perspective views of another example of an elongate member and a location device for use with the system of FIGS. 2A-2F, according to an aspect of the disclosure.
Figure 10B:
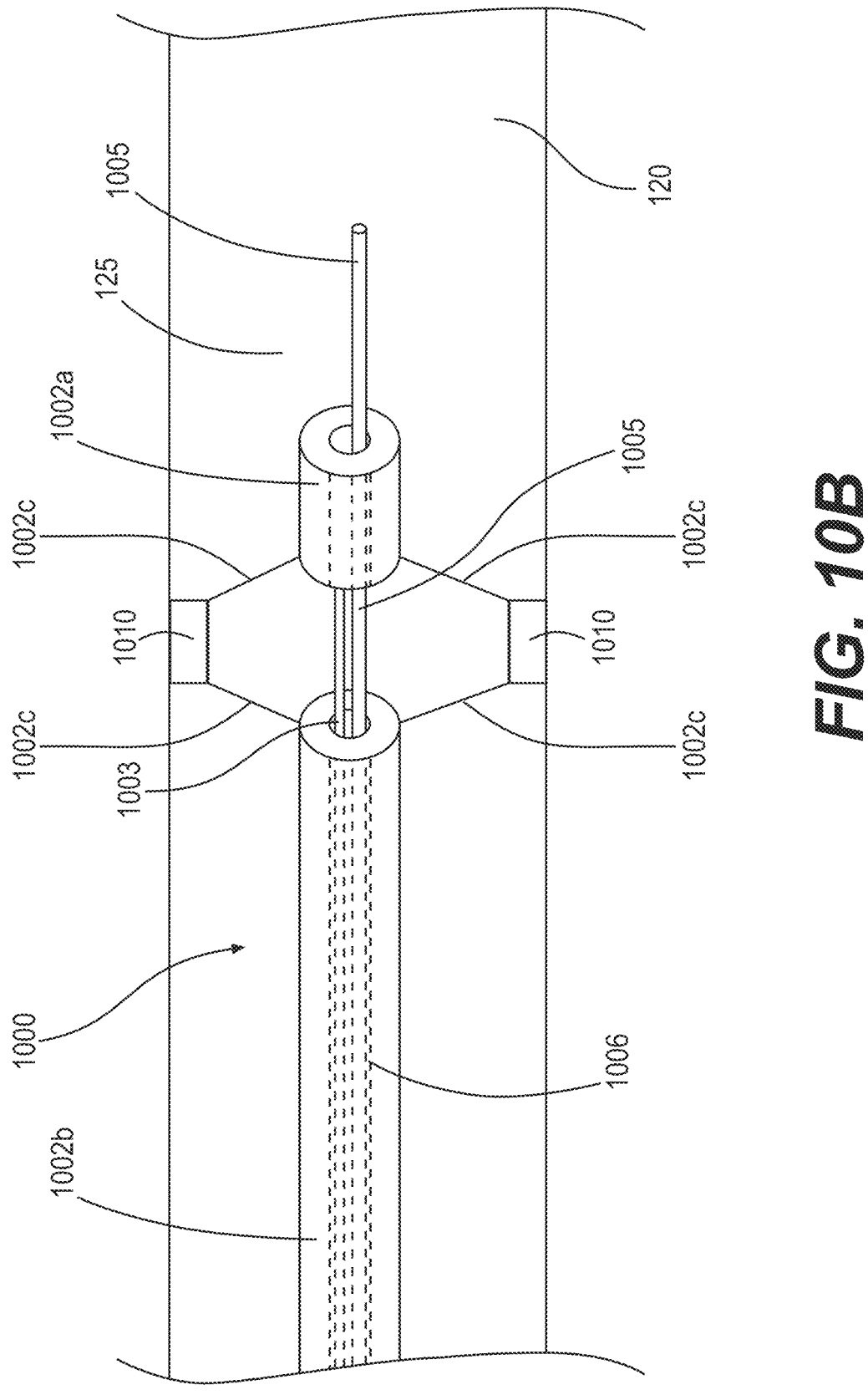

Another example of a location device 1000 is illustrated in FIGS. 10A and 10B. Similar to the location devices described herein, location device 1000 may be disposed at a distal end of a sheath 1002 (sheath may include any catheter or nasocatheter described herein). Sheath 1002 may include a central lumen 1006 through which a guidewire 1005 may extend. Sheath 1002 may include a distal tip 1002a connected to a sheath main body 1002b by a plurality of wires 1002c. Distal tip 1002a may be ring-like and may include a lumen (which may be an extension of central lumen 1006 from sheath main body 1002b) to track over guidewire 1005. Distal tip 1002a may have a same or different outer circumference as sheath main body 1002b. LEDs 1010 may be disposed on each of the plurality of wires 1002c. For example, each of the plurality of wires 1002c may include a green LED 1010 and a red LED 1010, or a plurality of green and red LEDs 1010. Alternatively, each of the plurality of wires 1002c may include only one LED 1010, and the color of LEDs 1010 may alternate about a circumference of sheath 1002. Alternatively, each LED 1010 may connect a proximal end of each wire 1002c to a respective distal end thereof. Wires 1002 may provide current/power to LEDs 1010. A tension wire 1003 may attach to and extend from distal tip 1002a, to a proximal end of sheath 1002. Wire 1003 may translate within lumen 1006 and may be actuated to move distal tip 1002a in a proximal direction and a distal direction. For example, when tension wire 1003 is moved proximally, distal tip 1002a is also moved in a proximal direction, causing the plurality of wires 1002c to bend radially outward from guidewire 1005. In this manner, LEDs 1010 located on the plurality of wires 1002c may be moved toward and pressed against a wall of jejunum 120.

A method of deploying location device 1010 will now be described. It will be understood that location device 1000 may be advanced to a target location in any manner described herein. Once location device 1010 is positioned within jejunum 120, a medical professional may control tension wire 1003 (e.g., pull wire 1003 proximally) to cause distal tip 1002a to move proximally while maintaining a fixed position of main body 1002b. This movement causes LEDs 1010 to move away from a longitudinal axis of sheath 1002 and presses or urges LEDs 1010 against the wall of jejunum 120. Location device 1000 may then be located and incisions in the walls of stomach 105 and jejunum 120 may be made in any manner described herein. After the incisions are formed, the medical professional may control tension wire 1003 (e.g., push wire 1003 distally) to cause distal tip 1002*a* to move distally while maintaining a fixed position of main body 1002*b*, causing LEDs 1010 to move radially inward and approach guidewire 1005. It will be understood that a position of distal tip 1002*a* may be maintained while moving main body 1002*b* in a proximal and/or distal direction. Once LEDs 1010 are no longer deployed, sheath 1002 may be removed from the patient.

Figure 11A:
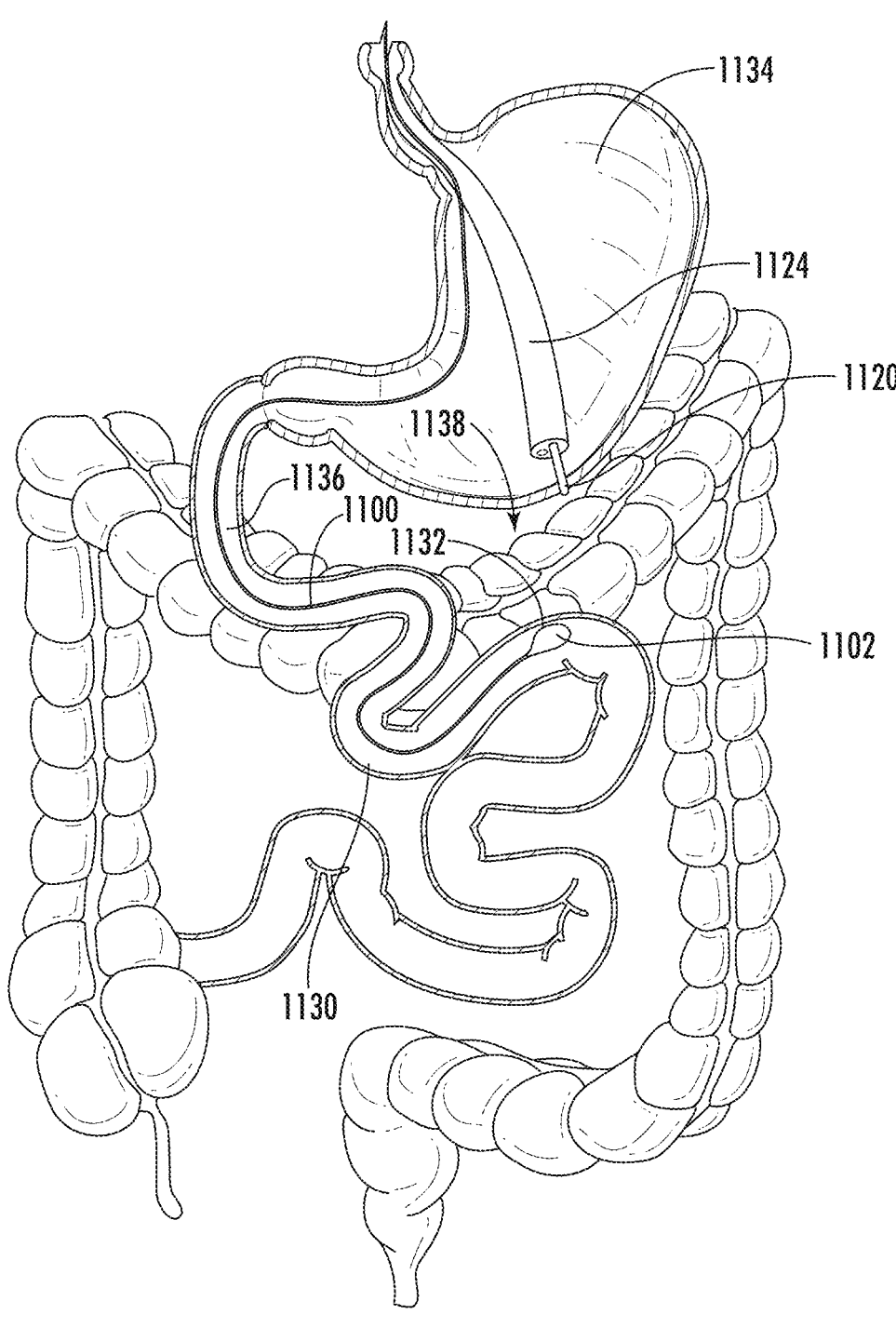
FIG. 11A illustrates an elongate member extending into the jejunum and an instrument extending through a wall of the stomach into the peritoneal cavity toward the elongate member, according to an aspect of the present disclosure.
Figure 11B:
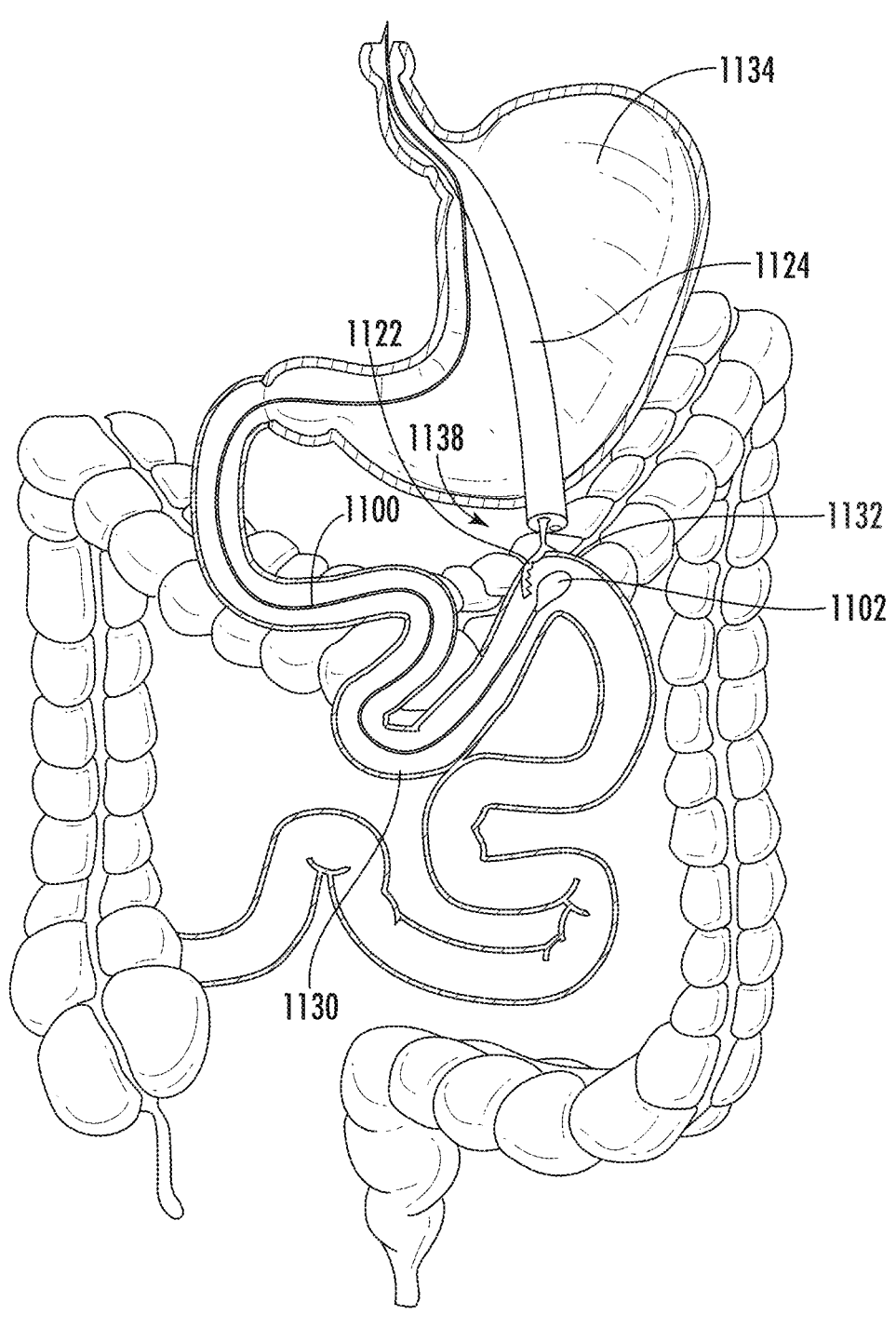
FIG. 11B illustrates the system of FIG. 11A with an instrument manipulating the jejunum.
Figure 11C:
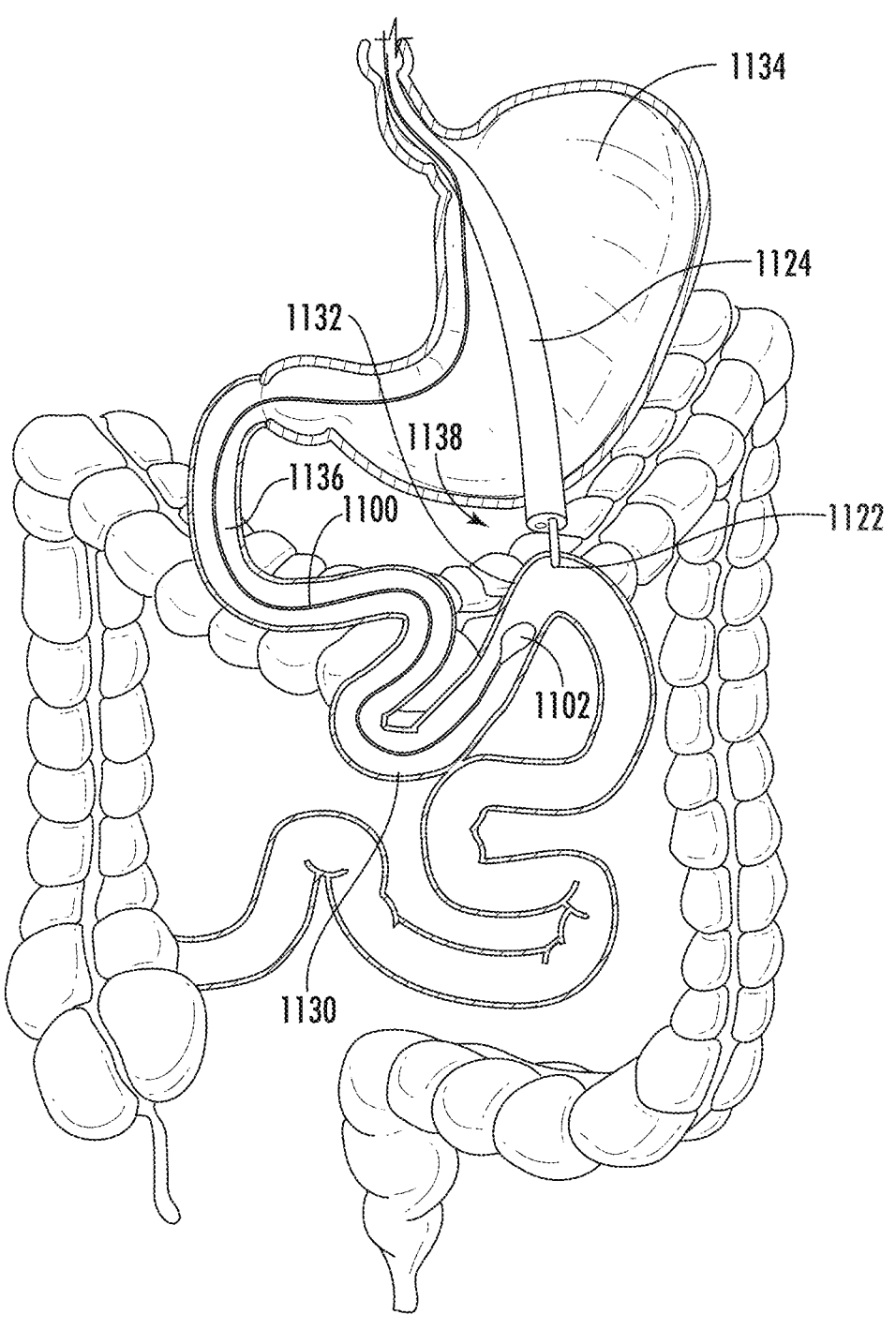
FIG. 11C illustrates the system of FIGS. 11A and 11B with an instrument extending through a wall of the jejunum.

In various procedures, a medical professional may have difficulty locating a portion of a body lumen containing a medical device locator. FIGS. 11A-11C illustrate a portion of a gastrojejunostomy procedure substantially similar to that of FIGS. 2B-2D. For example, in FIGS. 2C and 2D, the portion of the jejunum 120 containing the distal end 235 of the nasocatheter 230 may be difficult to locate after extending the distal end 245 of the endoscope 240 through the wall of the stomach 215 to view the small bowel 125. Similar difficulties of other procedures are contemplated related to locating devices and/or anatomy. FIGS. 11A-11C illustrate a portion of a procedure to locate a medical device locator at a target position within the jejunum. The medical device locator at the target position may be viewable by an instrument insertable through the stomach wall. Once viewed, the target location in the jejunum may be accessed by the instrument, and a stent or other drainage conduit may be placed bridging the stomach and the jejunum.

With reference to FIG. 11A, a sheath, a guidewire, or an elongate member 1100 is shown inserted into the GI tract through the stomach 1134 and extended into the duodenum 1136 and the jejunum 1130. An endoscope 1124 is shown extended within the stomach 1134 with a perforation or cutting mechanism 1120 extending distally out of a working channel of the endoscope 1124 toward a tissue wall of the stomach 1134. The perforation mechanism 1120 is shown making an incision into the wall of the stomach 1124 into the peritoneal cavity 1138 and generally toward a portion 1132 of the jejunum 1130 containing a location device 1102 at a distal end of the elongate member 1100 that is extended within the jejunum 1130.

Referring to FIG. 11B, the endoscope 1124 of the system of FIG. 11A is shown extended through the incision in the tissue wall of the stomach 1134 into the peritoneal cavity 1138. The endoscope 1124 is oriented generally toward the jejunum 1130 in the peritoneal cavity 1138. The medical professional may view the jejunum 1130 within the peritoneal cavity 1138 via the endoscope 1124 and/or through other observation techniques, e.g., fluoroscopy, or the like. The medical professional may observe the jejunum 1130 and identify a portion 1132 of the jejunum 1130 correlating with a location of the elongate member 1100 and/or the location device 1102 contained therein by any visual indicator described herein, e.g., illuminated LEDs. An end effector 1122 such as a grasper is shown grasping the portion 1132 of the jejunum 1130 such that the portion 1132 may be held in place, manipulated for incision, and/or manipulated toward the stomach 1134. In FIG. 11B, the portion 1132 is manipulated closer toward the stomach 1134 compared to the position in FIG. 11A.

Referring to FIG. 11C, the portion 1132 of the jejunum 1130 is shown manipulated into a position toward the stomach 1134 from FIGS. 11A and 11B. The perforation mechanism 1122 is shown making an incision into the portion 1132 of the jejunum 1130 and the location device 1102 has been proximally translated away from the portion 1132, avoiding collision and/or heat transfer from the perforation mechanism 1122. However, the location device 1102 may be left at the portion 1132 for the procedure. With an incision in the tissue wall of the stomach 1134 and in the tissue wall of the portion 1132 of the jejunum 1130, additional devices may be delivered to the tissue wall of the stomach 1134, the tissue wall of the jejunum 1130, and/or extending within the peritoneal cavity 1138 as described herein.

In various embodiments, an elongate member may be a catheter (e.g. a nasocatheter or the like), an endoscope, a guidewire, or a sheath extending about another medical device. An elongate member may have visual indicators along its length and its length may distally extend to a location device as described herein.

Figures 12, 13, 14:
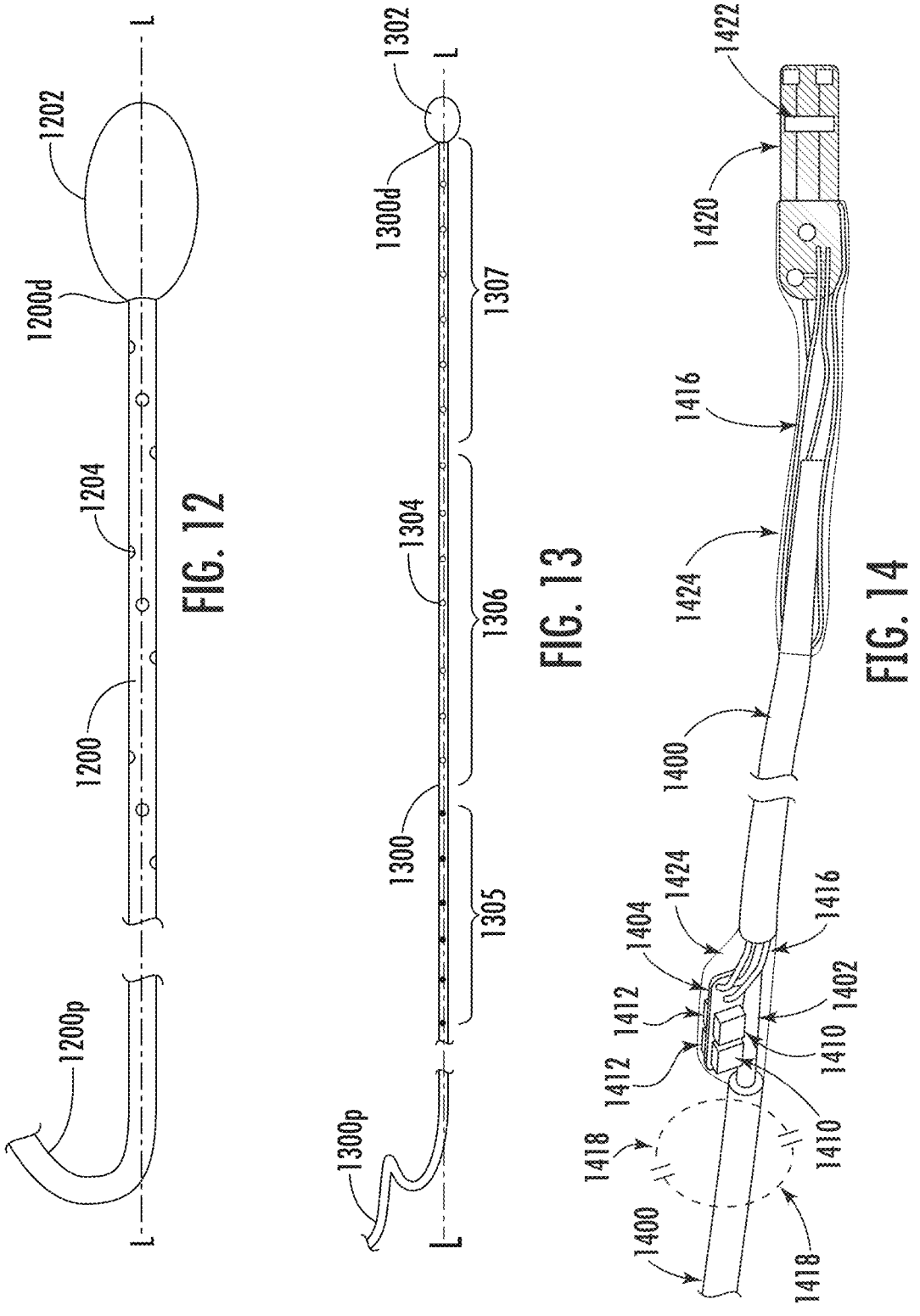
FIG. 12 illustrates an elongate member having a plurality of LEDs disposed along its length, according to an aspect of the present disclosure.
FIG. 13 illustrates an elongate member having a plurality of LEDs disposed along its length, according to an aspect of the present disclosure.
FIG. 14 illustrates an elongate member having a plurality of LEDs disposed along its length, according to an aspect of the present disclosure.

With reference to FIG. 12, an embodiment of a medical device locator is illustrated including a sheath, a guidewire, or an elongate member 1200 having a proximal end 1200*p*, a distal end 1200*d*, and a length extending along a longitudinal axis ℓ therethrough. LEDs 1204 are disposed along the length of the elongate member 1200. The LEDs 1204 are arranged helically about the longitudinal axis ℓ of the elongate member 1200. A location device 1202 is disposed at the distal end 1200*d* of the elongate member 1200.

In various embodiments, illuminating members, which may be LEDs, may extend along a portion of a length of an elongate member. The LEDs may extend to a distal end of the elongate member including a location device. The LEDs may be arranged in various patterns along the elongate member, e.g., helically, axially, radially, circumferentially, linearly, intermittently spaced, randomly, at various densities along the length, or a combination of arrangements thereof, or the like, such that the LEDs may be viewed from one or a multiple of radial viewing angles from a longitudinal axis of the elongate member. The LEDs may be actuated to emit light. Actuated LEDs may be viewable across a tissue wall, e.g., from outside of a body lumen containing the LEDs. The LEDs may have variable wavelengths such that they emit colors as an indicator that may be more easily viewable across a tissue wall than other colors, e.g., red, green, or the like, may be more viewable than other colors. The LEDs may be actuated at varying frequencies as an indicator. Indicators may designate a location, e.g., an indicator may be a certain distance from an end of an elongate member, a location device, or an anatomy. LEDS may be individually selectable and controllable as a single LED or in groups of more than a single LED. LEDs may be controllable by one or more parameters, such as density, location of the LEDS with respect to each other, anatomies or medical devices, size, shape, frequency of actuation (e.g., patterned to assist with locating or notifications such as double flashes followed by a pause), intensity of actuation (e.g., using a current source, e.g., with pulse width modulation (PWM) operating at a desired frequency and/or duty cycle affecting LED intensity), duration of actuation, color, or any combination of two or more of the foregoing.

In various embodiments, a controller may be electrically coupled to LEDs along an elongate member. Electrical leads may be interleaved in electrical communication with the LEDs such that the LEDs may be independently actuated. The controller may be configured to sequentially actuate one or more of the LEDs at a time. The controller may sequentially actuate the LEDs in a distal direction along a length of the elongate member, e.g., indicating a direction toward a distal end of the elongate member toward a location device. The controller may be configured to sequentially actuate the LEDs such that only a single LED or multiple LEDs is/are actuated at once, e.g., an actuation pattern of a distally travelling wave of illumination along the elongate member. The controller may be configured to actuate all of the LEDs except one LED in a distally sequential pattern such that a large number (e.g., more than 90% of all of the LEDs or the like) of the LEDs are actuated for location identification while still indicating a direction, e.g., an actuation pattern of a distally travelling wave of de-illumination along the elongate member. The controller may be configured to actuate the LEDs at a higher frequency with reduced illumination time (e.g., a lower duty cycle having a lower percentage of time that the LEDs are illuminated) to reduce heat compared to LEDs that are actuated at a lower frequency with a longer illumination time (e.g., a higher duty cycle having a larger percentage of time that the LEDs are illuminated). The controller may be configured to actuate a portion of the LEDs at a first frequency and another portion of the LEDs at a second frequency, e.g., a distal portion of LEDs at a higher frequency than a proximal portion of LEDs. The LEDs may extend along the length of the elongate member for a distance that substantially aligns with an anatomy of a patient. For example, the LEDs may extend along a length between the pylorus and the portion of the jejunum with the target location for the procedure. This may be any desired amount of length, e.g., about 50 centimeters distal to the pylorus, about 150 centimeters distal to the pylorus, or the like. The controller may be manually or automatically operated to actuate one or more LEDS or to switch between various patterns of operation. Such actuation of LEDs may be shortened to reduce heat.

With reference to FIG. 13, an embodiment of a medical device locator is illustrated including a sheath, a guidewire, or an elongate member 1300 having a proximal end 1300*p*, a distal end 1300*d*, and a length extending along a longitudinal axis ℓ therethrough. LEDs 1304 are disposed along the length of the elongate member 1300. The LEDs 1304 are arranged linearly about and along the longitudinal axis ℓ of the elongate member 1300. A location device 1302 is disposed at the distal end 1300*d* of the elongate member 1300. The LEDs are configured to emit variable wavelengths. A proximal portion 1305 of the LEDs 1304 are configured to emit a red wavelength of light, a mid portion 1306 of the LEDs 1304 are configured to emit a white wavelength of light, and a distal portion 1307 of the LEDs 1304 are configured to emit a green wavelength of light. The portions 1305, 1306, 1307 indicate a location along the elongate member 1300. The proximal portion 1305 indicates a location along the elongate member 1300 proximal to the mid portion 1306, which indicates a location along the elongate member 1300 proximal to the distal portion 1307, which indicates a location along the elongate member 1300 proximal to the distal end 1300*d* or location device 1302. The portions 1305, 1306, 1307 may each be located at varying distances from the distal end 1300*d* of the elongate member 1300, e.g., the proximal portion 1305 may be located about, e.g., 50 centimeters or the like from the distal end 1300*d*, the mid portion 1306 may be located about, e.g., 15 centimeters or the like from the distal end 1300*d*, and the distal portion 1307 may be located substantially at the distal end 1300*d*. Although three portions 1305, 1306, 1307 of LEDs 1304 and three colors are illustrated, any number and/or location of portions and/or colors may be employed.

With reference to FIG. 14, an embodiment of a medical device locator is illustrated including a sheath, a guidewire, or an elongate member 1400, which may be, e.g., a guidewire. The elongate member 1400 includes LEDs 1410, 1412 disposed along its length. A support member 1402 extends longitudinally within the elongate member 1400. A board 1404 is disposed along the support member 1402 such that the board 1404 extends radially away from the support member 1402. The LEDs 1410, 1412 are disposed on opposing sides of the board 1404 such that a first pair of LEDs 1410 are disposed on a first side of the board 1404 and a second pair of LEDs 1412 are disposed on a second side of the board 1404. The LEDs 1410, 1412 are arranged on opposing sides of the board 1404 such that at least a pair of LEDs 1410, 1412 are viewable in 180° arcs 1418 about the elongate member 1400. The pairs of LEDs 1410, 1412 may each include LEDs of variable colors, e.g., green and red, that may both be illuminated, selectively illuminated, alternatively illuminated, or sequentially illuminated to increase visibility (e.g., across tissue) and/or indicate orientation (e.g., green indicating a distal direction of the elongate member 1400 and red indicating a proximal direction of the elongate member 1400). Although pairs of LEDs 1410, 1412 are illustrated totaling four LEDs 1420, 1412, LEDs may be grouped in sections larger than pairs or not grouped at all, and any number of LEDs may be employed, e.g., 1, 2, 3, 5, 6, 8, 10, 15, 20, 50, 100, or the like. The LEDs 1410, 1412 may be illuminated and controlled by wire conduits 1416 electrically coupled to the LEDs 1410, 1412 and extending proximally within and along the elongate member 1400. The wires 1416 may extend proximally along the elongate member 1400 to a connector 1420. The connector 1420 may be reversibly coupled to a controller and may be sized to fit through a working channel of an endoscope. The controller may comprise, e.g., a power source, circuits, instructions and/or switches for powering and controlling illumination of the LEDs 1410, 1412, etc. The connector 1420 includes contacts 1422 in electrical communication with the wires 1416 and the contacts 1422 may be reversibly coupled to leads of the controller. Portions of the wires 1416 and LEDs that are externally exposed from the elongate member 1400 are covered by a transparent/translucent coating 1424 (e.g., silicone or the like) that protects the electrical connections between the LEDs 1410, 1412, the board 1404, the wires 1416, and the connector 1420 from external fluid/debris (e.g., bodily fluids) and trauma while allowing visibility of illuminated LEDs 1410, 1412.

In use, an endoscope having a working channel may be inserted into a duodenum of a patient and the elongate member 1400 may be extended through the working channel into the duodenum. The elongate member 1400 may be further advanced along the small bowel to a desired location that may be observed and measured by markings (e.g., radiopaque and/or colored markings) on the elongate member 1400 to indicate that the elongate member 1400 and/or the LEDs 1410, 1412 are at the desired distance beyond the pylorus (e.g., about 150 cm). The endoscope then may be proximally withdrawn along the elongate member 1400, leaving the elongate member 1400 in the small bowel. When the distal end of the endoscope is withdrawn to the pylorus, the elongate member 1400 may be proximally or distally adjusted, e.g., to place a marking of the elongate member 1400 at the pylorus. The endoscope may then be completely withdrawn from the patient along the elongate member 1400 and the connector 1420. The connector 1420 may then be coupled with the controller allowing operation of the LEDs 1410, 1412.

In general, as applicable to any of the locator devices and systems described above or otherwise within the present disclosure, an embodiment of a method of locating a medical device across a body lumen may include extending an elongate member comprising a plurality of LEDs along a length of the elongate member within a first body lumen, e.g., the jejunum, such as the steps for positioning the locator device of FIG. 14, as described above in the preceding paragraph. The plurality of LEDs may be actuated sequentially in a distal direction along the length of the elongate member. The sequentially actuated LEDs may indicate a direction of a device or an anatomy such as a location device and/or a portion of the first body lumen. The actuated LEDs may be viewed across a tissue wall of the first body lumen, for example, from within the peritoneal cavity. A perforation mechanism, e.g., a cutting tool, may be extended across a tissue wall of a second body lumen, e.g., the stomach, toward the first body lumen, cutting into a tissue wall of the first body lumen.

It will be apparent to those skilled in the art that various modifications and variations can be made to the disclosed device without departing from the scope of the disclosure. For example, the configuration of location devices and catheters, may be altered to suit any medical device or medical therapy. It will be understood that the number and/or location of LEDs is not limited to the examples described herein. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
an elongated member including a location device mounted on an outer surface of the elongated member, the location device including at least one light emitting diode (LED) emitting green light, and at least one separate LED emitting red light, the LED's controllable to emit the red light separately from the green light in a direction radially outwardly away from the outer surface of the elongated member to facilitate locating the location device by the red light or separately by the green light;
wherein:
the location device further includes a sidewall, a proximal end wall at a proximal end of the sidewall, and a distal end wall at a distal end of the sidewall;
the sidewall, the proximal end wall, and the distal end wall define a cavity; and
at least one of the LEDs is disposed within the cavity.

2. The medical device according to claim 1, wherein the sidewall includes a transparent material or a semi-transparent material.

3. The medical device according to claim 2, wherein at least one of the proximal end wall or the distal end wall includes one or more of an opaque material or a light attenuating material.

4. The medical device according to claim 3, further comprising a vacuum device and a fluid containment device, wherein each of the vacuum device and the fluid containment device are in fluid communication with the fluid lumen at the proximal end of the elongated member, and wherein the vacuum device is configured to create suction within the fluid lumen such that a fluid from a body is configured to flow through the plurality of holes and along the fluid lumen to the fluid containment device.

5. The medical device according to claim 1, wherein at least one of the proximal end wall or the distal end wall includes one or more of an opaque material or a light attenuating material.

6. The medical device according to claim 1, wherein the elongated member includes a fluid lumen extending from a proximal end of the elongated member to a distal end of the elongated member, and wherein a plurality of holes are in a sidewall of the elongated member and are fluidly connected to the fluid lumen.

7. The medical device according to claim 1, wherein the elongated member further includes a central lumen configured to receive a guidewire.

8. The medical device according to claim 1, further comprising a balloon disposed on a circumferentially opposite side of the cavity.

9. The medical device according to claim 1, wherein the elongated member includes an elongated member main body and an elongated member distal tip, wherein a proximal end of the elongated member distal tip is connected to a distal end of the elongated member main body by a plurality of wires, and wherein an LED is attached to each wire from the plurality of wires.

10. The medical device according to claim 1, wherein the LEDs are configured to alternatively emit light.

11. The medical device according to claim 10, further comprising an actuation wire attached to the elongated member distal tip, wherein the actuation wire is configured to move proximally relative to the elongated member main body, and wherein at least one of the LEDs is configured to move radially outward when the actuation wire moves the elongated member distal end proximally relative to the elongated member main body.

12. The medical device according to claim 1, wherein at least one of the LEDs is configured to emit light in a pulsed manner.

13. The medical device according to claim 1, further comprising an endoscope including an imaging device, and an end effector configured to extend from a distal end of the endoscope, wherein the imaging device is configured to detect the light having wavelengths corresponding to the green light and to the red light emitted from the LEDs.

14. A medical device comprising:
an elongated member including a location device at a distal end of the elongated member, the location device including at least one light emitting diode (LED) configured to be actuated to emit a light having a wavelength corresponding to a green light, and at least one LED configured to be actuated to emit a light having a wavelength corresponding to a red light;
wherein the elongated member includes a fluid lumen extending from a proximal end of the elongated member to a distal end of the elongated member, and wherein a plurality of holes are in a sidewall of the elongated member and are fluidly connected to the fluid lumen.

15. The medical device according to claim 14, further comprising a vacuum device and a fluid containment device, wherein each of the vacuum device and the fluid containment device are in fluid communication with the fluid lumen at the proximal end of the elongated member, and wherein the vacuum device is configured to create suction within the fluid lumen such that a fluid from a body is configured to flow through the plurality of holes and along the fluid lumen to the fluid containment device.

16. The medical device according to claim 14, wherein the holes are provided at the distal end of the elongated member, or along an intermediate length of the elongated member, or along a proximal length of the elongated member, or a combination thereof.

17. The medical device according to claim 14, wherein the holes are provided along a substantially same circumference of the elongated member and/or around a circumference of the elongated member.

18. A medical device comprising:

an elongated member including a location device at a distal end of the elongated member, the location device including at least one light emitting diode (LED) configured to be actuated to emit a light having a wavelength corresponding to a green light, and at least one LED configured to be actuated to emit a light having a wavelength corresponding to a red light; and an actuation wire attached to the elongated member distal tip, wherein the actuation wire is configured to move proximally and distally relative to the elongated member to move the at least one LED radially outward to be pressed against tissue.

19. The medical device according to claim 18, wherein:

the elongated member includes an elongated member main body and an elongated member distal tip; and movement of the actuation wire moves the elongated member distal end relative to the elongated member main body to cause the at least one LED to move radially outward.

20. The medical device according to claim 19, wherein proximal movement of the actuation wire moves the elongated member distal end proximally relative to the elongated member main body to cause the at least one LED to move radially outward.

\* \* \* \* \*